US008551696B2

(12) United States Patent
Scholz et al.

(10) Patent No.: US 8,551,696 B2

(45) **Date of Patent: *Oct. 8, 2013**

(54) RUBELLA E1 ENVELOPE PROTEIN VARIANTS AND THEIR USE IN DETECTION OF ANTI-RUBELLA ANTIBODIES

(75) Inventors: Christian Scholz, Penzberg (DE); Ralf Bollhagen, Penzberg (DE); Alfred Engel, Weilheim (DE); Elke Faatz, Huglfing (DE); Peter Schaarschmidt, Uffing (DE); Barbara Upmeier, Iffeldorf (DE); Toralf Zarnt, Iffeldorf (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 520 days.

This patent is subject to a terminal disclaimer.

(21) Appl. No.: 12/793,134

(22) Filed: Jun. 3, 2010

(65) Prior Publication Data

US 2011/0059552 A1 Mar. 10, 2011

Related U.S. Application Data

(63) Continuation of application No. PCT/EP2008/010532, filed on Dec. 11, 2008.

(30) Foreign Application Priority Data

Dec. 13, 2007 (EP) .................................... 07024190

(51) Int. Cl.

| | |
|---|---|
| ***C12Q 1/70*** | (2006.01) |
| ***A61K 39/20*** | (2006.01) |
| ***C12N 7/01*** | (2006.01) |

(52) U.S. Cl.

USPC ............ 435/5; 435/219; 435/235.1; 435/7.1; 530/826

(58) Field of Classification Search

None

See application file for complete search history.

(56) References Cited

U.S. PATENT DOCUMENTS 7,604,935 B2 * 10/2009 Upmeier et al. .................. 435/5

FOREIGN PATENT DOCUMENTS

EP 1780282 2/2007

EP 1780282 * 5/2007

OTHER PUBLICATIONS

Scholz et al, Biochemistry, 47:4276-4287 (2008).

Gros et al, Virology, 230:179-186 (1997), Article No. VY978462.

Starkey et al, Journal of Clinical Microbiology, 270-274 (Feb. 1995).

Scholz et al, Biochemistry, 45:20-33 (2006).

* cited by examiner

*Primary Examiner* — Zachariah Lucas

*Assistant Examiner* — Stuart W Snyder

(74) *Attorney, Agent, or Firm* — Roche Diagnostics Operations, Inc.

(57) ABSTRACT

The invention relates to soluble rubella E1 antigens and variants of these antigens. The antigens contain amino acids 201 to 432 or 169 to 432 and are lacking amino acids 453 to 481 as well as at least the amino acids 143 to 164. They further contain a region spanning two disulfide-bridges. The invention also relates to a recombinant DNA molecule encoding the rubella E1 antigens, the expression of rubella E1 antigens as chaperone fusion proteins and their use in a method of detecting antibodies against rubella in a sample.

7 Claims, 5 Drawing Sheets

1 EEAFTYLCTA PGCATQAPVP VRLAGVRFES KIVDGGCFAP WDLEATGACI CEIPTDVSCE 60

7 Y 8 9

61 GLGAWVPAAP CARIWNGTQR ACTFWAVNAY SSGGYAQLAS YFNPGGSYYK QYHPTACEVE 120

10 11Y

121 PAFGHSDAAC WGFPTDTVMS VFALASYVQH PHKTVRVKFH TETRTVWQLS VAGVSCNVTT 180

12 Y 13 14

181 EHPFCNTPHG QLEVQVPPDP GDLVEYIMNY TGNQQSRWGL CSPNCHGPDW ASPVCQRHSP 240

15 16

241 DCSRLVGATP ERPRLRLVDA DDPLLRTAPG PGEVWVTPVI GSQARKCGLH IRAGPYGHAT 300

17 18

301 VEMPEWIHAH TTSDPWHPPG PLGLKFKTVR PVALPRTLAP PRNVRVTGCY QCGTPALVEG 360

19 20

361 LAPGGGNCHL TVNGEDLGAV PPGKFVTAAL LNTPPPYQVS CGGESDRATA RVIDPAAQSF 420

21 22 24

421 TGVVYGTHTT AVSETRQ*TWA EWAAAHWWQL TL*GAICALPL AGLLACCAKC LYYLRGAIAP 480

Table 3. Immunological reactivities of C-terminal Rubella E1 (201-432) variants with various disulfide bridge combinations

| | E1 (201-432) C17-C18 C19-C20 | E1 (201-432) C13-C14 C17-C18 C19-C20 | E1 (201-432) C13-C14 C17-C18 | E1 (201-432) C13-C14 | E1 (201-432) C17-C18 | E1 (201-432) C19-C20 | E1 (201-432) no disulfide |
|---|---|---|---|---|---|---|---|
| Rubella negative sera average counts | 2,830 | 4,610 | 2,072 | 2,076 | 1,453 | 2,487 | 2,076 |
| Rubella positive sera | relative signal | relative signal | relative signal | relative signal | relative signal | relative signal | relative signal |
| BRK 01/2003_106 | 72.1 | 185.6 | 334.1 | 196.0 | 2.5 | 4.2 | 1.2 |
| BRK 01/2003_107 | 151.8 | 126.2 | 50.5 | 2.0 | 1.4 | 5.9 | 0.7 |
| BRK 01/2003_111 | 12.6 | 13.9 | 17.4 | 5.8 | 2.3 | 1.3 | 1.1 |
| BRK 01/2003_121 | 69.0 | 69.3 | 160.3 | 118.1 | 220.5 | 119.9 | 93.8 |
| BRK 01/2003_129 | 17.8 | 19.4 | 26.3 | 6.6 | 2.2 | 2.5 | 1.2 |
| BRK 01/2003_147 | 50.4 | 46.3 | 43.0 | 5.7 | 3.9 | 2.9 | 1.5 |
| BRK 01/2003_149 | 18.8 | 26.1 | 46.7 | 14.9 | 1.8 | 2.0 | 0.9 |
| BRK 01/2003_152 | 6.9 | 7.0 | 10.7 | 2.1 | 2.1 | 1.0 | 1.0 |
| BRK 01/2003_153 | 53.8 | 51.5 | 68.4 | 17.9 | 6.3 | 6.3 | 3.2 |
| BRK 01/2003_154 | 101.6 | 95.0 | 58.3 | 7.6 | 5.5 | 10.0 | 2.8 |

Figure 4

Table 4. Immunological reactivities of C-terminal Rubella E1 (169-432 and 201-432) variants with various disulfide bridge combinations

| | E1 (169-432) no disulfide | E1 (169-432) C11-C12 | E1 (169-432) C11-C12 C17-C18 | E1 (169-432) C11-C12 C19-C20 | E1 (169-432) C11-C12 C13-C14 | E1 (169-432) C11-C12 C17-C18 C19-C20 | E1 (201-432) C13-C14 C19-C20 | E1 (201-432) C17-C18 C19-C20 |
|---|---|---|---|---|---|---|---|---|
| Rubella negative sera average counts | 5,017 | 2,606 | 3,319 | 4,562 | 2,008 | 2,746 | 1,709 | 2,675 |
| Rubella positive sera | relative signal | relative signal | relative signal | relative signal | relative signal | relative signal | relative signal | relative signal |
| BRK 01/2003_106 | 1.0 | 1.5 | 1.3 | 5.8 | 309.3 | 96.0 | 325.7 | 71.9 |
| BRK 01/2003_107 | 0.6 | 0.7 | 0.6 | 8.6 | 3.1 | 151.7 | 14.5 | 137.7 |
| BRK 01/2003_111 | 1.2 | 1.6 | 1.5 | 1.7 | 9.4 | 16.8 | 9.8 | 12.7 |
| BRK 01/2003_121 | 53.1 | 104.8 | 85.1 | 52.4 | 130.9 | 70.9 | 120.1 | 53.2 |
| BRK 01/2003_129 | 0.9 | 1.2 | 1.1 | 2.8 | 11.4 | 25.0 | 13.9 | 17.6 |
| BRK 01/2003_147 | 1.4 | 2.0 | 1.8 | 4.7 | 9.5 | 61.2 | 12.9 | 48.4 |
| BRK 01/2003_149 | 0.7 | 0.9 | 0.9 | 3.3 | 23.0 | 27.5 | 27.0 | 18.1 |
| BRK 01/2003_152 | 0.9 | 1.2 | 1.0 | 1.2 | 3.2 | 9.9 | 3.6 | 6.6 |
| BRK 01/2003_153 | 2.5 | 4.4 | 3.8 | 7.1 | 28.9 | 70.1 | 34.5 | 50.1 |
| BRK 01/2003_154 | 2.3 | 4.0 | 3.3 | 11.9 | 12.9 | 136.4 | 26.7 | 102.9 |
| BRK 01/2003_119 | 0.8 | 1.1 | 0.9 | 8.3 | 21.9 | 66.9 | 35.8 | 40.7 |
| BRK 01/2003_123 | 2.7 | 3.7 | 3.4 | 8.7 | 15.6 | 98.3 | 25.4 | 73.5 |
| BRK 01/2003_127 | 1.6 | 3.0 | 2.5 | 4.0 | 19.2 | 43.4 | 21.0 | 34.5 |
| BRK 01/2003_130 | 1.1 | 1.4 | 1.3 | 1.8 | 20.0 | 13.1 | 21.4 | 9.4 |

L = $(GGGS)_5$GGG-Linker

SEQUENCE LISTING

<160> NUMBER OF SEQ ID NOS: 13

<210> SEQ ID NO 1
<211> LENGTH: 232
<212> TYPE: PRT
<213> ORGANISM: Rubella virus

<400> SEQUENCE: 1

```
Gly Asp Leu Val Glu Tyr Ile Met Asn Tyr Thr Gly Asn Gln Gln Ser
1               5                   10                  15

Arg Trp Gly Leu Gly Ser Pro Asn Cys His Gly Pro Asp Trp Ala Ser
            20                  25                  30

Pro Val Cys Gln Arg His Ser Pro Asp Cys Ser Arg Leu Val Gly Ala
        35                  40                  45

Thr Pro Glu Arg Pro Arg Leu Arg Leu Val Asp Ala Asp Asp Pro Leu
    50                  55                  60

Leu Arg Thr Ala Pro Gly Pro Gly Glu Val Trp Val Thr Pro Val Ile
65                  70                  75                  80

Gly Ser Gln Ala Arg Lys Cys Gly Leu His Ile Arg Ala Gly Pro Tyr
                85                  90                  95

Gly His Ala Thr Val Glu Met Pro Glu Trp Ile His Ala His Thr Thr
            100                 105                 110

Ser Asp Pro Trp His Pro Pro Gly Pro Leu Gly Leu Lys Phe Lys Thr
        115                 120                 125

Val Arg Pro Val Ala Leu Pro Arg Thr Leu Ala Pro Pro Arg Asn Val
    130                 135                 140

Arg Val Thr Gly Cys Tyr Gln Cys Gly Thr Pro Ala Leu Val Glu Gly
145                 150                 155                 160

Leu Ala Pro Gly Gly Gly Asn Cys His Leu Thr Val Asn Gly Glu Asp
                165                 170                 175

Leu Gly Ala Val Pro Pro Gly Lys Phe Val Thr Ala Ala Leu Leu Asn
            180                 185                 190

Thr Pro Pro Pro Tyr Gln Val Ser Cys Gly Gly Glu Ser Asp Arg Ala
        195                 200                 205

Thr Ala Arg Val Ile Asp Pro Ala Ala Gln Ser Phe Thr Gly Val Val
    210                 215                 220

Tyr Gly Thr His Thr Thr Ala Val
225                 230
```

<210> SEQ ID NO 2
<211> LENGTH: 264
<212> TYPE: PRT
<213> ORGANISM: Rubella virus

<400> SEQUENCE: 2

```
Leu Ser Val Ala Gly Val Ser Cys Asn Val Thr Thr Glu His Pro Phe
1               5                   10                  15

Cys Asn Thr Pro His Gly Gln Leu Glu Val Gln Val Pro Pro Asp Pro
            20                  25                  30

Gly Asp Leu Val Glu Tyr Ile Met Asn Tyr Thr Gly Asn Gln Gln Ser
        35                  40                  45

Arg Trp Gly Leu Gly Ser Pro Asn Cys His Gly Pro Asp Trp Ala Ser
    50                  55                  60

Pro Val Cys Gln Arg His Ser Pro Asp Cys Ser Arg Leu Val Gly Ala
65                  70                  75                  80
```

-continued

```
Thr Pro Glu Arg Pro Arg Leu Arg Leu Val Asp Ala Asp Asp Pro Leu
                85                  90                  95

Leu Arg Thr Ala Pro Gly Pro Gly Glu Val Trp Val Thr Pro Val Ile
            100                 105                 110

Gly Ser Gln Ala Arg Lys Cys Gly Leu His Ile Arg Ala Gly Pro Tyr
        115                 120                 125

Gly His Ala Thr Val Glu Met Pro Glu Trp Ile His Ala His Thr Thr
    130                 135                 140

Ser Asp Pro Trp His Pro Pro Gly Pro Leu Gly Leu Lys Phe Lys Thr
145                 150                 155                 160

Val Arg Pro Val Ala Leu Pro Arg Thr Leu Ala Pro Pro Arg Asn Val
                165                 170                 175

Arg Val Thr Gly Cys Tyr Gln Cys Gly Thr Pro Ala Leu Val Glu Gly
            180                 185                 190

Leu Ala Pro Gly Gly Gly Asn Cys His Leu Thr Val Asn Gly Glu Asp
        195                 200                 205

Leu Gly Ala Val Pro Pro Gly Lys Phe Val Thr Ala Ala Leu Leu Asn
    210                 215                 220

Thr Pro Pro Pro Tyr Gln Val Ser Cys Gly Gly Glu Ser Asp Arg Ala
225                 230                 235                 240

Thr Ala Arg Val Ile Asp Pro Ala Ala Gln Ser Phe Thr Gly Val Val
                245                 250                 255

Tyr Gly Thr His Thr Thr Ala Val
            260


<210> SEQ ID NO 3
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rubella E1 antigen; several Cys residues
      substituted by Ala

<400> SEQUENCE: 3

Gly Asp Leu Val Glu Tyr Ile Met Asn Tyr Thr Gly Asn Gln Gln Ser
1               5                   10                  15

Arg Trp Gly Leu Gly Ser Pro Asn Ala His Gly Pro Asp Trp Ala Ser
            20                  25                  30

Pro Val Ala Gln Arg His Ser Pro Asp Ala Ser Arg Leu Val Gly Ala
        35                  40                  45

Thr Pro Glu Arg Pro Arg Leu Arg Leu Val Asp Ala Asp Asp Pro Leu
    50                  55                  60

Leu Arg Thr Ala Pro Gly Pro Gly Glu Val Trp Val Thr Pro Val Ile
65                  70                  75                  80

Gly Ser Gln Ala Arg Lys Ala Gly Leu His Ile Arg Ala Gly Pro Tyr
                85                  90                  95

Gly His Ala Thr Val Glu Met Pro Glu Trp Ile His Ala His Thr Thr
            100                 105                 110

Ser Asp Pro Trp His Pro Pro Gly Pro Leu Gly Leu Lys Phe Lys Thr
        115                 120                 125

Val Arg Pro Val Ala Leu Pro Arg Thr Leu Ala Pro Pro Arg Asn Val
    130                 135                 140

Arg Val Thr Gly Cys Tyr Gln Cys Gly Thr Pro Ala Leu Val Glu Gly
145                 150                 155                 160
```

```
Leu Ala Pro Gly Gly Gly Asn Cys His Leu Thr Val Asn Gly Glu Asp
                165                 170                 175

Leu Gly Ala Val Pro Pro Gly Lys Phe Val Thr Ala Ala Leu Leu Asn
            180                 185                 190

Thr Pro Pro Pro Tyr Gln Val Ser Cys Gly Gly Glu Ser Asp Arg Ala
        195                 200                 205

Thr Ala Arg Val Ile Asp Pro Ala Ala Gln Ser Phe Thr Gly Val Val
    210                 215                 220

Tyr Gly Thr His Thr Thr Ala Val
225                 230


<210> SEQ ID NO 4
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rubella E1 with mutations; several Cys residues
      replaced by Ala

<400> SEQUENCE: 4

Gly Asp Leu Val Glu Tyr Ile Met Asn Tyr Thr Gly Asn Gln Gln Ser
1               5                   10                  15

Arg Trp Gly Leu Gly Ser Pro Asn Cys His Gly Pro Asp Trp Ala Ser
            20                  25                  30

Pro Val Cys Gln Arg His Ser Pro Asp Ala Ser Arg Leu Val Gly Ala
        35                  40                  45

Thr Pro Glu Arg Pro Arg Leu Arg Leu Val Asp Ala Asp Asp Pro Leu
    50                  55                  60

Leu Arg Thr Ala Pro Gly Pro Gly Glu Val Trp Val Thr Pro Val Ile
65                  70                  75                  80

Gly Ser Gln Ala Arg Lys Ala Gly Leu His Ile Arg Ala Gly Pro Tyr
                85                  90                  95

Gly His Ala Thr Val Glu Met Pro Glu Trp Ile His Ala His Thr Thr
            100                 105                 110

Ser Asp Pro Trp His Pro Pro Gly Pro Leu Gly Leu Lys Phe Lys Thr
        115                 120                 125

Val Arg Pro Val Ala Leu Pro Arg Thr Leu Ala Pro Pro Arg Asn Val
    130                 135                 140

Arg Val Thr Gly Cys Tyr Gln Cys Gly Thr Pro Ala Leu Val Glu Gly
145                 150                 155                 160

Leu Ala Pro Gly Gly Gly Asn Ala His Leu Thr Val Asn Gly Glu Asp
                165                 170                 175

Leu Gly Ala Val Pro Pro Gly Lys Phe Val Thr Ala Ala Leu Leu Asn
            180                 185                 190

Thr Pro Pro Pro Tyr Gln Val Ser Ala Gly Gly Glu Ser Asp Arg Ala
        195                 200                 205

Thr Ala Arg Val Ile Asp Pro Ala Ala Gln Ser Phe Thr Gly Val Val
    210                 215                 220

Tyr Gly Thr His Thr Thr Ala Val
225                 230


<210> SEQ ID NO 5
<211> LENGTH: 232
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: Rubella E1 with mutations; several Cys residues
      replaced by Ala

<400> SEQUENCE: 5

```
Gly Asp Leu Val Glu Tyr Ile Met Asn Tyr Thr Gly Asn Gln Gln Ser
1               5                   10                  15

Arg Trp Gly Leu Gly Ser Pro Asn Cys His Gly Pro Asp Trp Ala Ser
            20                  25                  30

Pro Val Cys Gln Arg His Ser Pro Asp Ala Ser Arg Leu Val Gly Ala
        35                  40                  45

Thr Pro Glu Arg Pro Arg Leu Arg Leu Val Asp Ala Asp Asp Pro Leu
    50                  55                  60

Leu Arg Thr Ala Pro Gly Pro Gly Glu Val Trp Val Thr Pro Val Ile
65                  70                  75                  80

Gly Ser Gln Ala Arg Lys Ala Gly Leu His Ile Arg Ala Gly Pro Tyr
                85                  90                  95

Gly His Ala Thr Val Glu Met Pro Glu Trp Ile His Ala His Thr Thr
            100                 105                 110

Ser Asp Pro Trp His Pro Pro Gly Pro Leu Gly Leu Lys Phe Lys Thr
        115                 120                 125

Val Arg Pro Val Ala Leu Pro Arg Thr Leu Ala Pro Pro Arg Asn Val
    130                 135                 140

Arg Val Thr Gly Ala Tyr Gln Ala Gly Thr Pro Ala Leu Val Glu Gly
145                 150                 155                 160

Leu Ala Pro Gly Gly Gly Asn Cys His Leu Thr Val Asn Gly Glu Asp
                165                 170                 175

Leu Gly Ala Val Pro Pro Gly Lys Phe Val Thr Ala Ala Leu Leu Asn
            180                 185                 190

Thr Pro Pro Pro Tyr Gln Val Ser Cys Gly Gly Glu Ser Asp Arg Ala
        195                 200                 205

Thr Ala Arg Val Ile Asp Pro Ala Ala Gln Ser Phe Thr Gly Val Val
    210                 215                 220

Tyr Gly Thr His Thr Thr Ala Val
225                 230
```

<210> SEQ ID NO 6
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rubella E1 with mutations; several Cys residues
      replaced by Ala

<400> SEQUENCE: 6

```
Leu Ser Val Ala Gly Val Ser Cys Asn Val Thr Thr Glu His Pro Phe
1               5                   10                  15

Cys Asn Thr Pro His Gly Gln Leu Glu Val Gln Val Pro Pro Asp Pro
            20                  25                  30

Gly Asp Leu Val Glu Tyr Ile Met Asn Tyr Thr Gly Asn Gln Gln Ser
        35                  40                  45

Arg Trp Gly Leu Gly Ser Pro Asn Cys His Gly Pro Asp Trp Ala Ser
    50                  55                  60

Pro Val Cys Gln Arg His Ser Pro Asp Ala Ser Arg Leu Val Gly Ala
```

```
65                  70                  75                  80

Thr Pro Glu Arg Pro Arg Leu Arg Leu Val Asp Ala Asp Asp Pro Leu
                85                  90                  95

Leu Arg Thr Ala Pro Gly Pro Gly Glu Val Trp Val Thr Pro Val Ile
            100                 105                 110

Gly Ser Gln Ala Arg Lys Ala Gly Leu His Ile Arg Ala Gly Pro Tyr
        115                 120                 125

Gly His Ala Thr Val Glu Met Pro Glu Trp Ile His Ala His Thr Thr
    130                 135                 140

Ser Asp Pro Trp His Pro Pro Gly Pro Leu Gly Leu Lys Phe Lys Thr
145                 150                 155                 160

Val Arg Pro Val Ala Leu Pro Arg Thr Leu Ala Pro Pro Arg Asn Val
                165                 170                 175

Arg Val Thr Gly Ala Tyr Gln Ala Gly Thr Pro Ala Leu Val Glu Gly
            180                 185                 190

Leu Ala Pro Gly Gly Gly Asn Ala His Leu Thr Val Asn Gly Glu Asp
        195                 200                 205

Leu Gly Ala Val Pro Pro Gly Lys Phe Val Thr Ala Ala Leu Leu Asn
    210                 215                 220

Thr Pro Pro Pro Tyr Gln Val Ser Ala Gly Gly Glu Ser Asp Arg Ala
225                 230                 235                 240

Thr Ala Arg Val Ile Asp Pro Ala Ala Gln Ser Phe Thr Gly Val Val
                245                 250                 255

Tyr Gly Thr His Thr Thr Ala Val
            260


<210> SEQ ID NO 7
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rubella E1 with mutations; several Cys replaced
      by Ala

<400> SEQUENCE: 7

Leu Ser Val Ala Gly Val Ser Cys Asn Val Thr Thr Glu His Pro Phe
1               5                   10                  15

Cys Asn Thr Pro His Gly Gln Leu Glu Val Gln Val Pro Pro Asp Pro
            20                  25                  30

Gly Asp Leu Val Glu Tyr Ile Met Asn Tyr Thr Gly Asn Gln Gln Ser
        35                  40                  45

Arg Trp Gly Leu Gly Ser Pro Asn Ala His Gly Pro Asp Trp Ala Ser
    50                  55                  60

Pro Val Ala Gln Arg His Ser Pro Asp Ala Ser Arg Leu Val Gly Ala
65                  70                  75                  80

Thr Pro Glu Arg Pro Arg Leu Arg Leu Val Asp Ala Asp Asp Pro Leu
                85                  90                  95

Leu Arg Thr Ala Pro Gly Pro Gly Glu Val Trp Val Thr Pro Val Ile
            100                 105                 110

Gly Ser Gln Ala Arg Lys Ala Gly Leu His Ile Arg Ala Gly Pro Tyr
        115                 120                 125

Gly His Ala Thr Val Glu Met Pro Glu Trp Ile His Ala His Thr Thr
    130                 135                 140

Ser Asp Pro Trp His Pro Pro Gly Pro Leu Gly Leu Lys Phe Lys Thr
```

```
145                 150                 155                 160

Val Arg Pro Val Ala Leu Pro Arg Thr Leu Ala Pro Pro Arg Asn Val
                165                 170                 175

Arg Val Thr Gly Cys Tyr Gln Cys Gly Thr Pro Ala Leu Val Glu Gly
            180                 185                 190

Leu Ala Pro Gly Gly Gly Asn Ala His Leu Thr Val Asn Gly Glu Asp
        195                 200                 205

Leu Gly Ala Val Pro Pro Gly Lys Phe Val Thr Ala Ala Leu Leu Asn
    210                 215                 220

Thr Pro Pro Pro Tyr Gln Val Ser Ala Gly Gly Glu Ser Asp Arg Ala
225                 230                 235                 240

Thr Ala Arg Val Ile Asp Pro Ala Ala Gln Ser Phe Thr Gly Val Val
                245                 250                 255

Tyr Gly Thr His Thr Thr Ala Val
            260


<210> SEQ ID NO 8
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rubella E1 with mutations; several Cys replaced
      by Ala

<400> SEQUENCE: 8

Leu Ser Val Ala Gly Val Ser Cys Asn Val Thr Thr Glu His Pro Phe
1               5                   10                  15

Cys Asn Thr Pro His Gly Gln Leu Glu Val Gln Val Pro Pro Asp Pro
            20                  25                  30

Gly Asp Leu Val Glu Tyr Ile Met Asn Tyr Thr Gly Asn Gln Gln Ser
        35                  40                  45

Arg Trp Gly Leu Gly Ser Pro Asn Ala His Gly Pro Asp Trp Ala Ser
    50                  55                  60

Pro Val Ala Gln Arg His Ser Pro Asp Ala Ser Arg Leu Val Gly Ala
65                  70                  75                  80

Thr Pro Glu Arg Pro Arg Leu Arg Leu Val Asp Ala Asp Asp Pro Leu
                85                  90                  95

Leu Arg Thr Ala Pro Gly Pro Gly Glu Val Trp Val Thr Pro Val Ile
            100                 105                 110

Gly Ser Gln Ala Arg Lys Ala Gly Leu His Ile Arg Ala Gly Pro Tyr
        115                 120                 125

Gly His Ala Thr Val Glu Met Pro Glu Trp Ile His Ala His Thr Thr
    130                 135                 140

Ser Asp Pro Trp His Pro Pro Gly Pro Leu Gly Leu Lys Phe Lys Thr
145                 150                 155                 160

Val Arg Pro Val Ala Leu Pro Arg Thr Leu Ala Pro Pro Arg Asn Val
                165                 170                 175

Arg Val Thr Gly Ala Tyr Gln Ala Gly Thr Pro Ala Leu Val Glu Gly
            180                 185                 190

Leu Ala Pro Gly Gly Gly Asn Cys His Leu Thr Val Asn Gly Glu Asp
        195                 200                 205

Leu Gly Ala Val Pro Pro Gly Lys Phe Val Thr Ala Ala Leu Leu Asn
    210                 215                 220

Thr Pro Pro Pro Tyr Gln Val Ser Cys Gly Gly Glu Ser Asp Arg Ala
```

```
225                 230                 235                 240

Thr Ala Arg Val Ile Asp Pro Ala Ala Gln Ser Phe Thr Gly Val Val
                245                 250                 255

Tyr Gly Thr His Thr Thr Ala Val
            260


<210> SEQ ID NO 9
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rubella E1 with mutations; several Cys replaced
      by Ala

<400> SEQUENCE: 9

Leu Ser Val Ala Gly Val Ser Cys Asn Val Thr Thr Glu His Pro Phe
1               5                   10                  15

Cys Asn Thr Pro His Gly Gln Leu Glu Val Gln Val Pro Pro Asp Pro
            20                  25                  30

Gly Asp Leu Val Glu Tyr Ile Met Asn Tyr Thr Gly Asn Gln Gln Ser
        35                  40                  45

Arg Trp Gly Leu Gly Ser Pro Asn Ala His Gly Pro Asp Trp Ala Ser
    50                  55                  60

Pro Val Ala Gln Arg His Ser Pro Asp Ala Ser Arg Leu Val Gly Ala
65                  70                  75                  80

Thr Pro Glu Arg Pro Arg Leu Arg Leu Val Asp Ala Asp Asp Pro Leu
                85                  90                  95

Leu Arg Thr Ala Pro Gly Pro Gly Glu Val Trp Val Thr Pro Val Ile
            100                 105                 110

Gly Ser Gln Ala Arg Lys Ala Gly Leu His Ile Arg Ala Gly Pro Tyr
        115                 120                 125

Gly His Ala Thr Val Glu Met Pro Glu Trp Ile His Ala His Thr Thr
    130                 135                 140

Ser Asp Pro Trp His Pro Pro Gly Pro Leu Gly Leu Lys Phe Lys Thr
145                 150                 155                 160

Val Arg Pro Val Ala Leu Pro Arg Thr Leu Ala Pro Pro Arg Asn Val
                165                 170                 175

Arg Val Thr Gly Cys Tyr Gln Cys Gly Thr Pro Ala Leu Val Glu Gly
            180                 185                 190

Leu Ala Pro Gly Gly Gly Asn Cys His Leu Thr Val Asn Gly Glu Asp
        195                 200                 205

Leu Gly Ala Val Pro Pro Gly Lys Phe Val Thr Ala Ala Leu Leu Asn
    210                 215                 220

Thr Pro Pro Pro Tyr Gln Val Ser Cys Gly Gly Glu Ser Asp Arg Ala
225                 230                 235                 240

Thr Ala Arg Val Ile Asp Pro Ala Ala Gln Ser Phe Thr Gly Val Val
                245                 250                 255

Tyr Gly Thr His Thr Thr Ala Val
            260


<210> SEQ ID NO 10
<211> LENGTH: 264
<212> TYPE: PRT
<213> ORGANISM: Artificial Sequence
<220> FEATURE:
<223> OTHER INFORMATION: Description of Artificial Sequence: Synthetic
```

polypeptide
<220> FEATURE:
<223> OTHER INFORMATION: Rubella E1 with mutations; several Cys residues replaced by Ala

<400> SEQUENCE: 10

Leu Ser Val Ala Gly Val Ser Cys Asn Val Thr Thr Glu His Pro Phe
1 5 10 15

Cys Asn Thr Pro His Gly Gln Leu Glu Val Gln Val Pro Pro Asp Pro
20 25 30

Gly Asp Leu Val Glu Tyr Ile Met Asn Tyr Thr Gly Asn Gln Gln Ser
35 40 45

Arg Trp Gly Leu Gly Ser Pro Asn Cys His Gly Pro Asp Trp Ala Ser
50 55 60

Pro Val Cys Gln Arg His Ser Pro Asp Ala Ser Arg Leu Val Gly Ala
65 70 75 80

Thr Pro Glu Arg Pro Arg Leu Arg Leu Val Asp Ala Asp Asp Pro Leu
85 90 95

Leu Arg Thr Ala Pro Gly Pro Gly Glu Val Trp Val Thr Pro Val Ile
100 105 110

Gly Ser Gln Ala Arg Lys Ala Gly Leu His Ile Arg Ala Gly Pro Tyr
115 120 125

Gly His Ala Thr Val Glu Met Pro Glu Trp Ile His Ala His Thr Thr
130 135 140

Ser Asp Pro Trp His Pro Pro Gly Pro Leu Gly Leu Lys Phe Lys Thr
145 150 155 160

Val Arg Pro Val Ala Leu Pro Arg Thr Leu Ala Pro Pro Arg Asn Val
165 170 175

Arg Val Thr Gly Cys Tyr Gln Cys Gly Thr Pro Ala Leu Val Glu Gly
180 185 190

Leu Ala Pro Gly Gly Gly Asn Ala His Leu Thr Val Asn Gly Glu Asp
195 200 205

Leu Gly Ala Val Pro Pro Gly Lys Phe Val Thr Ala Ala Leu Leu Asn
210 215 220

Thr Pro Pro Pro Tyr Gln Val Ser Ala Gly Gly Glu Ser Asp Arg Ala
225 230 235 240

Thr Ala Arg Val Ile Asp Pro Ala Ala Gln Ser Phe Thr Gly Val Val
245 250 255

Tyr Gly Thr His Thr Thr Ala Val
260

<210> SEQ ID NO 11
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Rubella E1 with mutations; several Cys residues replaced by Ala

<400> SEQUENCE: 11

Gly Asp Leu Val Glu Tyr Ile Met Asn Tyr Thr Gly Asn Gln Gln Ser
1 5 10 15

Arg Trp Gly Leu Gly Ser Pro Asn Cys His Gly Pro Asp Trp Ala Ser
20 25 30

Pro Val Cys Gln Arg His Ser Pro Asp Ala Ser Arg Leu Val Gly Ala
35 40 45

```
Thr Pro Glu Arg Pro Arg Leu Arg Leu Val Asp Ala Asp Asp Pro Leu
    50                  55                  60

Leu Arg Thr Ala Pro Gly Pro Gly Glu Val Trp Val Thr Pro Val Ile
65                  70                  75                  80

Gly Ser Gln Ala Arg Lys Ala Gly Leu His Ile Arg Ala Gly Pro Tyr
                85                  90                  95

Gly His Ala Thr Val Glu Met Pro Glu Trp Ile His Ala His Thr Thr
            100                 105                 110

Ser Asp Pro Trp His Pro Pro Gly Pro Leu Gly Leu Lys Phe Lys Thr
        115                 120                 125

Val Arg Pro Val Ala Leu Pro Arg Thr Leu Ala Pro Pro Arg Asn Val
    130                 135                 140

Arg Val Thr Gly Cys Tyr Gln Cys Gly Thr Pro Ala Leu Val Glu Gly
145                 150                 155                 160

Leu Ala Pro Gly Gly Gly Asn Cys His Leu Thr Val Asn Gly Glu Asp
                165                 170                 175

Leu Gly Ala Val Pro Pro Gly Lys Phe Val Thr Ala Ala Leu Leu Asn
            180                 185                 190

Thr Pro Pro Pro Tyr Gln Val Ser Cys Gly Gly Glu Ser Asp Arg Ala
        195                 200                 205

Thr Ala Arg Val Ile Asp Pro Ala Ala Gln Ser Phe Thr Gly Val Val
    210                 215                 220

Tyr Gly Thr His Thr Thr Ala Val
225                 230


<210> SEQ ID NO 12
<211> LENGTH: 481
<212> TYPE: PRT
<213> ORGANISM: Rubella virus

<400> SEQUENCE: 12

Glu Glu Ala Phe Thr Tyr Leu Cys Thr Ala Pro Gly Cys Ala Thr Gln
1               5                   10                  15

Ala Pro Val Pro Val Arg Leu Ala Gly Val Arg Phe Glu Ser Lys Ile
            20                  25                  30

Val Asp Gly Gly Cys Phe Ala Pro Trp Asp Leu Glu Ala Thr Gly Ala
        35                  40                  45

Cys Ile Cys Glu Ile Pro Thr Asp Val Ser Cys Glu Gly Leu Gly Ala
    50                  55                  60

Trp Val Pro Ala Ala Pro Cys Ala Arg Ile Trp Asn Gly Thr Gln Arg
65                  70                  75                  80

Ala Cys Thr Phe Trp Ala Val Asn Ala Tyr Ser Ser Gly Gly Tyr Ala
                85                  90                  95

Gln Leu Ala Ser Tyr Phe Asn Pro Gly Gly Ser Tyr Tyr Lys Gln Tyr
            100                 105                 110

His Pro Thr Ala Cys Glu Val Glu Pro Ala Phe Gly His Ser Asp Ala
        115                 120                 125

Ala Cys Trp Gly Phe Pro Thr Asp Thr Val Met Ser Val Phe Ala Leu
    130                 135                 140

Ala Ser Tyr Val Gln His Pro His Lys Thr Val Arg Val Lys Phe His
145                 150                 155                 160

Thr Glu Thr Arg Thr Val Trp Gln Leu Ser Val Ala Gly Val Ser Cys
                165                 170                 175

Asn Val Thr Thr Glu His Pro Phe Cys Asn Thr Pro His Gly Gln Leu
            180                 185                 190
```

Glu Val Gln Val Pro Pro Asp Pro Gly Asp Leu Val Glu Tyr Ile Met
195 200 205

Asn Tyr Thr Gly Asn Gln Gln Ser Arg Trp Gly Leu Gly Ser Pro Asn
210 215 220

Cys His Gly Pro Asp Trp Ala Ser Pro Val Cys Gln Arg His Ser Pro
225 230 235 240

Asp Cys Ser Arg Leu Val Gly Ala Thr Pro Glu Arg Pro Arg Leu Arg
245 250 255

Leu Val Asp Ala Asp Asp Pro Leu Leu Arg Thr Ala Pro Gly Pro Gly
260 265 270

Glu Val Trp Val Thr Pro Val Ile Gly Ser Gln Ala Arg Lys Cys Gly
275 280 285

Leu His Ile Arg Ala Gly Pro Tyr Gly His Ala Thr Val Glu Met Pro
290 295 300

Glu Trp Ile His Ala His Thr Thr Ser Asp Pro Trp His Pro Pro Gly
305 310 315 320

Pro Leu Gly Leu Lys Phe Lys Thr Val Arg Pro Val Ala Leu Pro Arg
325 330 335

Thr Leu Ala Pro Pro Arg Asn Val Arg Val Thr Gly Cys Tyr Gln Cys
340 345 350

Gly Thr Pro Ala Leu Val Glu Gly Leu Ala Pro Gly Gly Gly Asn Cys
355 360 365

His Leu Thr Val Asn Gly Glu Asp Leu Gly Ala Val Pro Pro Gly Lys
370 375 380

Phe Val Thr Ala Ala Leu Leu Asn Thr Pro Pro Pro Tyr Gln Val Ser
385 390 395 400

Cys Gly Gly Glu Ser Asp Arg Ala Thr Ala Arg Val Ile Asp Pro Ala
405 410 415

Ala Gln Ser Phe Thr Gly Val Val Tyr Gly Thr His Thr Thr Ala Val
420 425 430

Ser Glu Thr Arg Gln Thr Trp Ala Glu Trp Ala Ala Ala His Trp Trp
435 440 445

Gln Leu Thr Leu Gly Ala Ile Cys Ala Leu Pro Leu Ala Gly Leu Leu
450 455 460

Ala Cys Cys Ala Lys Cys Leu Tyr Tyr Leu Arg Gly Ala Ile Ala Pro
465 470 475 480

Arg

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Gly Gly Gly Ser Gly Gly Gly Ser Gly Gly Gly Ser Gly Gly Gly Ser
1 5 10 15

Gly Gly Gly Ser Gly Gly Gly
20

RUBELLA E1 ENVELOPE PROTEIN VARIANTS AND THEIR USE IN DETECTION OF ANTI-RUBELLA ANTIBODIES

RELATED APPLICATIONS

This application is a continuation of PCT/EP2008/010532 filed Dec. 11, 2008 which claims priority to EP 07024190.6 filed Dec. 13, 2007.

SEQUENCE LISTING

The instant application contains a Sequence Listing which has been submitted via EFS-Web and is hereby incorporated by reference in its entirety. Said ASCII copy, created on May 27, 2010, is named 24647US.txt, and is 30,613 bytes in size.

FIELD OF THE INVENTION

The invention relates to recombinant rubella E1 antigens and variants thereof. The antigens comprise amino acids 201 to 432 or 169 to 432 and are characterized by lacking at least the C-terminal transmembrane region and the anchor segment (amino acids 453 to 481) as well as at least the amino acids 143 to 164. The antigens further contain two disulfide-bridges, i.e., they contain the region from the disulfide bridge Cys 225-Cys 235 to Cys 349-Cys 352 or the region from Cys 225-Cys 235 to Cys 368-Cys 401 or the region from Cys 176-Cys 186 to Cys 225-Cys 235 or the region from Cys 176-Cys 185 to Cys 349-Cys 352 or the region from Cys 176-Cys 185 to Cys 368-Cys 401. The invention also relates to the production of these double disulfide bridge antigens and their use in a method of detecting anti-rubella antibodies in human sera. It is an important goal in the development of antigen reagents for an immunoassay intended for the detection of immunoglobulins to provide as many native-like stable epitopes as possible. A further aspect of the invention is therefore a composition comprising at least two rubella E1 antigens each of which contains at least two disulfide bridges, whereby the disulfide bond combinations within the various antigens differ from each other.

BACKGROUND OF THE INVENTION

Rubella virus is the only member of the Rubivirus genus within the Togaviridae family. The small enveloped (+) RNA virus is a human pathogen and causes a mild, self-limiting childhood disease (German measles or rubella) characterized by rash, lymphadenopathy and low-grade fever. When acquired in the first trimester of pregnancy, however, it may cause stillbirth, spontaneous abortion or several anomalies associated with the congenital rubella syndrome. The characteristic triad of congenital rubella syndrome includes cataracts, heart defects and deafness of the fetus. It necessitates rubella vaccination programs and surveillance of the immune status of women in child-bearing age.

The structural proteins of the rubella virus originate from a single 110 kDa polypeptide precursor, which is proteolytically cleaved to yield the capsid protein C and the envelope proteins E2 and E1. E2 and E1 are glycosylated, they form non-covalent heterodimers at the surface of the virion and are the preferred targets of the humoral immune response. The membrane-anchored ectodomain of the E1 protein, in particular, is immunodominant, and antibodies against E1 are abundant in sera from rubella-infected individuals.

The rubella E1 protein, also termed rubella hemagglutinin (see FIG. 1), presumably consists of a large ectodomain (residues 1-452), followed by a single transmembrane helix (residues 453-468) and a short cytoplasmic tail (residues 469-481). The residues 438-452, which immediately precede the transmembrane region, probably form also a helix. The ectodomain of E1 bears 20 cysteine residues, which are engaged in ten disulfide bonds. The cysteine pairs C(1)-C(2), C(3)-C(15), C(6)-C(7), C(9)C(10), C(11)-C(12), C(13)-C(14), C(17)-C(18) and C(19)-C(20) could be confirmed with certainty, whereas the pairing of the cysteine residues C(4), C(5), C(8) and C(16) remains ambiguous (Gros et al. 1997, Virology 230, 179-186). The ectodomain is glycosylated at the three asparagines 76, 177 and 209.

There have been several attempts in prior art to produce the rubella E1 protein for diagnostic purposes. Initially, soluble fragments of E1 to be used as antigens for immunoassays were isolated from the supernatant of infected Baby hamster kidney (BHK-21) or Vero cells. Later, various expression and secretion systems were developed with the aim of producing soluble and immunoreactive versions of E1 in eukaryotic hosts (Hobman et al. 1994, Virus Res. 31, 277-289 and Seto et al. 1994, J. Med. Virol. 44, 192-199). A glycosylated and soluble form of full-length E1 could be produced in baculovirus-infected *Spodoptera frugiperda* (Seppänen et al. 1991, J. Clin. Microbiol. 29, 1877-1882 and Oker-Blom 1989, Virology 172, 82-91) and CHO cells (Perrenoud et al. 2004, Vaccine 23, 480-488) and, most recently, in *Pichia pastoris* (Wen and Wang 2005, Intervirology 48, 321-328). The expression of rubella-like particles in BHK cells (Grangeot-Keros et al. J. lin. Microbiol. 33, 2392-2394) and in a stably transfected CHO cell line (Giessauf et al. 2005, Arch. Virol. 150, 2077-2090) yielded rubella antigens suitable for diagnostic purposes. These rubella-like particles are non-infectious, ill-defined agglomerates of the covalently linked rubella proteins C, E2 and E1, and are useful for detecting immunoglobulins of the M and G type.

Non-glycosylated forms of E1 could, in principle, be produced much more efficiently in a prokaryotic host. In an early attempt, a full-length and a truncated version (207-353) of rubella E1 were fused to protein A from *Staphylococcus aureus* and produced in *E. coli* (Terry et al. 1989, Arch. Virol. 104, 63-75). These fusion proteins were active as antigens, but not well soluble and therefore only of limited value for the specific detection of anti-E1 antibodies. In general, variants of E1 from prokaryotic hosts showed a strong tendency to aggregate, possibly because they are unglycosylated, or because they are incorrectly disulfide-bonded. In fusion with glutathione-S-transferase, only small fragments of E1 comprising as little as 75 or 44 amino acid residues could be expressed in a soluble and functional form (Newcombe et al. 1994, Clinical and Diagnostic Virology 2, 149-163 and Starkey et al. 1995, J. Clin. Microbiol. 33, 270-274). Larger E1 fragments encompassing 82 or 171 amino acid residues could be obtained when fused to both RecA and β-galactosidase (Wolinsky et al. 1991, J. Virol. 65, 3986-3994).

The oxidative refolding of large cysteine-rich proteins such as E1 is very difficult, because misfolded intermediates with wrong disulfides, which are trapped during refolding, have a very high tendency to aggregate. Therefore, many efforts concentrated on finding contiguous B-cell epitopes along the E1 polypeptide chain and to use corresponding short soluble peptides as antigens in immunoassays. Antibodies generally show modest affinities towards small peptide antigens, and therefore it remains a major aim to produce stable and soluble fragments of E1 with a high antigenicity and in high amounts, ideally by the massive production as inclusion bodies in a prokaryotic host, followed by a robust renaturation procedure.

In Newcombe et al., (supra) glutathione-S-transferase (GST) E1 fusion proteins were used to produce rubella E1 antigen fragments in *E. coli* in a soluble form. However, only after a substantial truncation of the E1 sequence a soluble expression was feasible for the cysteine-free region 243-286 (44 amino acid residues). European Patent Application EP-A-0299673 discloses a peptide from amino acid residues 207-353 which retains rubella Ig specific binding characteristics.

Furthermore, Starkey et al., (supra) disclose that a very short segment of 44 to 75 amino acid residues of rubella E1 was soluble when fused to GST. GST fusion proteins containing the entire E1 sequence as well as large E1 subfragments were expressed as insoluble inclusion bodies which could neither be purified nor renatured and were therefore discarded.

European patent application No. EP-A-1780282 discloses the recombinant expression and production of soluble rubella E1 envelope antigens that are characterized by lacking at least the C-terminal transmembrane region and the anchor segment as well as at least the segment from amino acids 143 to 164 in the middle part of the molecule. These rubella E1 antigens contain at least the region spanning the disulfide bridges Cys 349-Cys 352 and Cys 368-Cys 401 and optionally Cys 225-Cys 235. According to the teaching of EP-A-1782082 it is essential to have both disulfide bridges in the C-terminal part of the antigen intact, i.e., closed, to obtain a rubella E1 variant that is sufficiently antigenic and suitable for the detection of antibodies against rubella virus in a sample.

The problem to be solved was therefore to generate soluble rubella E1 variants which harbor further combinations of disulfide-stabilized epitopes and which are highly soluble and highly reactive in terms of immunology (i.e. highly antigenic), and therefore well-suited as antigens for diagnostic applications.

SUMMARY OF THE INVENTION

The invention relates to rubella E1 antigens and variants of these antigens. The antigens comprise amino acids 201 to 432 or 169 to 432 and are characterized by lacking at least the C-terminal transmembrane region and the anchor segment (amino acids 453 to 481) as well as at least the segment from amino acids 143 to 164 in the middle part of the molecule. They further contain a region spanning two disulfide-bridges, i.e. the region from the disulfide bridge Cys 225-Cys 235 to Cys 349-Cys 352 or the region from Cys 225-Cys 235 to Cys 368-Cys 401 or the region from Cys 176-Cys 185 to Cys 225-Cys 235 or the region from Cys 176-Cys 185 to Cys 349-Cys 352 or the region from Cys 176-Cys 185 to Cys 368-Cys 401. The invention also relates to a composition comprising at least two of these rubella E1 antigens as well as to the production of these double disulfide bridge antigens and their use in a method of detecting antibodies against rubella in a sample.

Preferably, the rubella E1 antigens are further characterized in that they lack at the C-terminal end the alpha-helical region comprising the amino acids residues 438 to 452.

The invention also relates to a composition comprising at least two rubella E1 antigens each of which comprises amino acids 201 to 432 or 169 to 432 with the proviso that each of said antigens lacks sequences corresponding to amino acids 143 to 164 and 454 to 481 of the native rubella E1 antigen and wherein each of the rubella E1 antigens contains two disulfide bridges in different combinations.

In addition, the invention relates to a recombinant DNA molecule encoding said rubella E1 antigen. Preferably the rubella E1 antigen is recombinantly expressed, more preferably it is expressed as a chaperone fusion protein. The invention also relates to an expression vector containing operably linked or integrated the above-described DNA encoding a rubella E1 antigen. The invention also concerns a host cell transformed with said expression vector and also a method for producing a soluble and immuno-reactive rubella E1 antigen, preferably a fusion protein containing an E1 part and a chaperone part, most preferably a chaperone belonging to the class of peptidyl prolyl isomerases.

The present invention discloses a method for the detection of anti-rubella antibodies in a human sample wherein the rubella E1 antigen is used as a binding partner for the anti-rubella antibodies. The invention comprises further a diagnostic test and a reagent kit for the detection of anti-rubella antibodies, containing at least one of the rubella E1 antigens.

BRIEF DESCRIPTION OF THE DRAWINGS

FIG. 2 shows the amino acid sequence of the E1 envelope protein from the rubella Therien strain (Dominguez et al. 1990, Virology 177, 225-238) (SEQ ID NO: 12). After processing of the 110 kDa precursor polypeptide, the mature E1 comprises 481 residues. A putative transmembrane segment 453-468 (bold letters on gray background) anchors the E1 ectodomain (1-452) to the viral surface. The adjacent putative helical segment 438-452 is italicized. The twenty four cysteine residues within E1 are marked with bold type C and numbered contiguously according to Gros et al. (supra). Important disulfide bonds within the soluble N- and C-fragments of E1 are boxed. The N fragment 1-133 (light gray) and the C fragment 201-432 (dark gray) were expressed in fusion with tandem SlyD* in *E. coli* and refolded from inclusion bodies to yield soluble E1 antigens.

FIG. 3 shows the assessment of various rubella E1 antigens for their ability to specifically detect anti-rubella immunoglobulins in human sera. The immunoassays were performed by using an ELECSYS 2010 analyzer (Roche Diagnostics GmbH) as described in Example 6. The relative signals are normalized relative to the average value obtained for seven rubella-negative samples. The rubella-positive sera were purchased from the Bavarian Red Cross (Germany) and the rubella-negative controls were purchased from Trina International Bioreactives AG (Switzerland). All E1 variants were soluble SlyD-SlyD fusion proteins, and their respective disulfide bond combinations are given in brackets (contiguous numbering of the cysteine residues within the E1 molecule). All sera classified as positive were confirmed as being correct.

FIG. 4 shows further experimental results of an immunoassay setup designed for detecting antibodies against rubella virus in human sera. The immunoassays were performed by using an ELECSYS 2010 analyzer as described in Example 6. The relative signals are normalized relative to the average value obtained for seven rubella-negative samples. The rubella-positive sera were purchased from the Bavarian Red Cross (Germany) and the rubella-negative controls were purchased from Trina International Bioreactives AG (Switzerland). All E1 variants were soluble SlyD-SlyD fusion proteins, and their respective disulfide combinations are given in brackets (contiguous numbering of the cysteine residues within the E1 molecule). All sera classified as positive were confirmed as being correct.

DETAILED DESCRIPTION OF THE INVENTION

The invention relates to a soluble and immunoreactive (i.e. antigenic) rubella E1 fragment that comprises an E1 polypeptide segment from amino acids 169 to 432 and bears two disulfide bridges.

The rubella E1 antigens according to the invention comprise amino acids 201 to 432 and are characterized by lacking at least the C-terminal transmembrane region and the anchor segment as well as at least the segment from amino acids 143 to 164 in the middle part of the molecule, i.e., a rubella E1 antigen is claimed with the proviso that said rubella E1 antigen lacks sequences corresponding to amino acids 143 to 164 and 454 to 481 of the mature or native-like folded rubella E1 antigen and contains two disulfide bridges, wherein a) one disulfide bridge is formed between Cys 225 and Cys 235 (C13-C14) and a second disulfide bridge is formed between Cys 349 and Cys 352 (C17-C18) or b) one disulfide bridge is formed between Cys 225 and Cys 235 (C13-C14) and a second disulfide bridge is formed between Cys 368 and Cys 401 (C19-C20).

Further rubella E1 antigens according to the invention comprise E1 amino acids 169 to 432, and are also characterized by lacking at least the C-terminal transmembrane region and the anchor segment as well as at least the segment from amino acids 143 to 164 in the middle part of the molecule, i.e., a rubella E1 antigen is claimed with the proviso that said rubella E1 antigen lacks sequences corresponding to amino acids 143 to 164 and 454 to 481 of the mature or native-like folded rubella E1 antigen and contains two disulfide bridges, wherein a) one disulfide bridge is formed between Cys 176 and Cys 185 (C11-C12) and a second disulfide bridge is formed between Cys 225 and Cys 235 (C13-C14) or b) one disulfide bridge is formed between Cys 176 and Cys 185 (C11-C12) and a second disulfide bridge is formed between Cys 349 and Cys 352 (C17-C18) or c) one disulfide bridge is formed between Cys 176 and Cys 185 (C11-C12) and a second disulfide bridge is formed between Cys 368 and Cys 401 (C19-C20).

A further embodiment of the invention is a rubella E1 antigen which comprises amino acids 169 to 432, and is characterized by lacking at least the C-terminal transmembrane region and the anchor segment as well as at least the segment from amino acids 143 to 164 in the middle part of the molecule, i.e., a rubella E1 antigen is claimed with the proviso that said rubella E1 antigen lacks sequences corresponding to amino acids 143 to 164 and 454 to 481 of the native rubella E1 antigen, wherein a disulfide bridge is formed between Cys 176 and Cys 185.

Figure 1:
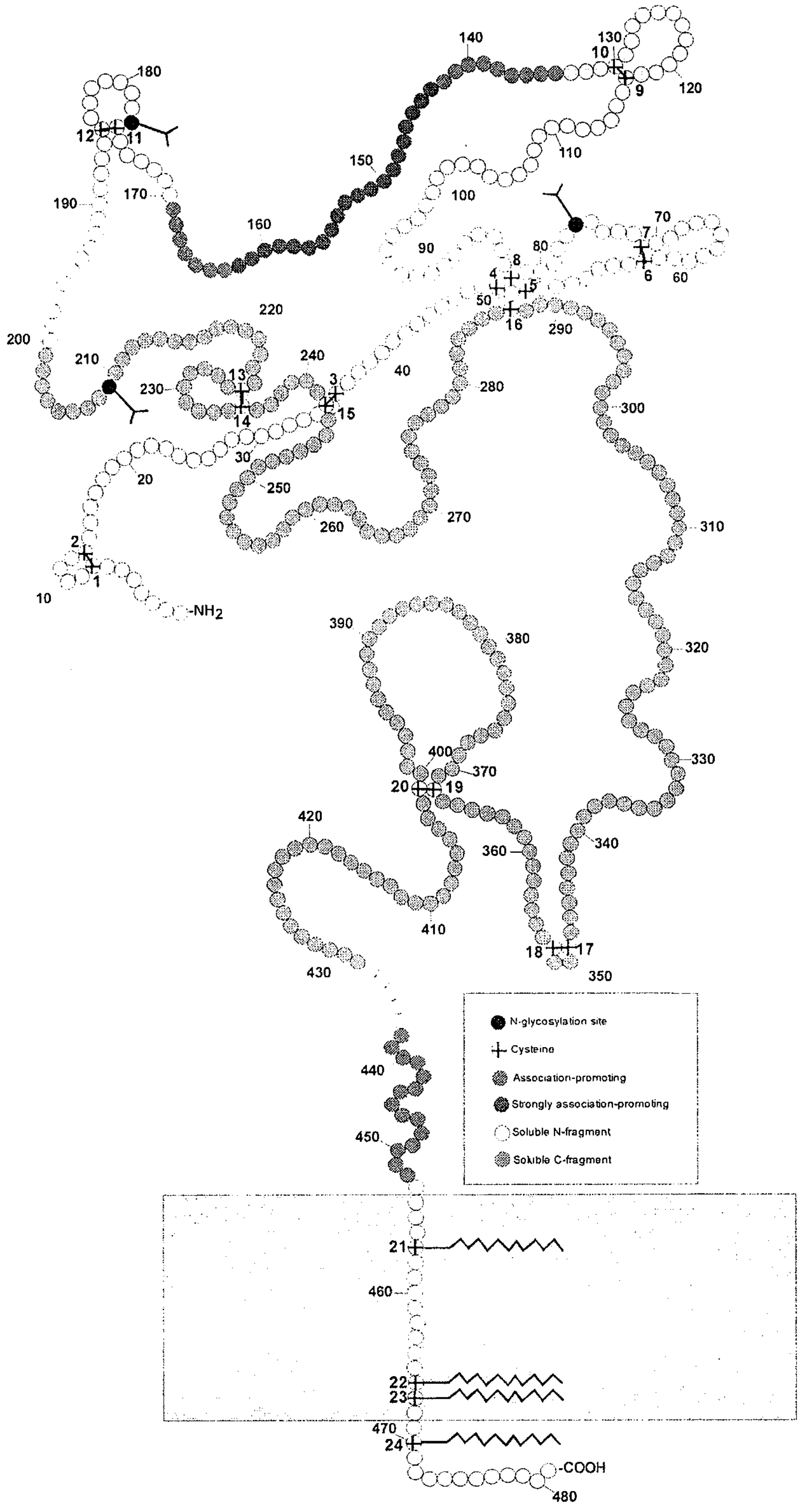
FIG. 1 shows a topology scheme of the membrane-anchored rubella E1 protein adapted from Gros et al. (1997, Virology 230, 179-186). The twenty four cysteine residues are numbered contiguously according to Gros et al. They are depicted as white circles with a black cross. The three N-glycosylation sites of mature viral E1 are coloured in black and marked with Y. Disulfide pairings as assigned by Gros et al. are highlighted by adjacent cysteines looping out the intervening sequence regions. The soluble N-fragment of E1 is marked with light gray circles, the soluble C-fragment of E1 is marked with gray circles. The strongly aggregation-promoting region between amino acids 143 and 162 is marked with dark gray circles, the modestly aggregation-promoting regions 134-142 and 163-168 are marked with gray circles. The putative membrane-adjacent helical region 438-452 is depicted as gray circles in a helix-like arrangement.

The numbering of the disulfide bridges given above refers to FIG. 1 and corresponds to cysteine residues C11-C12 (Cys 176-Cys 185), C13-C14 (Cys 225-Cys 235), C17-C18 (Cys 349-Cys 352) and C19-C20 (Cys 368-Cys 401). According to the contiguous numbering of cysteine residues a preferred rubella E1 antigen with two disulfide bridges thus comprises the disulfide bond combinations C13-C14 and C17-C18, or C13-C14 and C19-C20, or C13-C14 and C11-C12, or C19-C12 and C17-C18, or C11-C12 and C19-C20.

A preferred rubella E1 antigen comprises the E1 polypeptide fragment from amino acid 201 to 432 (201-432) and bears the disulfide bridges C13-C14 and C17-C18, i.e., the disulfide bridges Cys 225-Cys 235 and Cys 349-Cys 352. A further preferred rubella E1 antigen harbors the same disulfide combination in an E1 polypeptide fragment comprising the E1 amino acid sequence 169-432.

Preferably, the rubella E1 antigens according to the invention are further characterized in that they lack at the C-terminal end the putative alpha-helical region, which has been confined to amino acid residues 438 to 452 (Gros et al., 1997, Virology 230, 179-186).

According to the invention the rubella E1 antigens preferably contain combinations of two disulfide bridges. This means that not more than two disulfide bridges are formed within one rubella E1 antigen. In order to ensure a defined disulfide bond combination within rubella E1 antigen, all cysteine residues of the mature E1 that do not participate in the desired disulfide bonding are replaced by another amino acid similar to cysteine in size and structure. Preferably, these unwanted cysteine residues are substituted by alanine or serine. As a consequence, the substituted amino acid residues neither form abortive disulfide bridges nor contribute to detrimental side reactions such as disulfide shuffling. The desired matching cysteine pairs are supposed to be arranged in close vicinity during the in vitro refolding process, so that they can easily build the correct disulfide bonds and thus stabilize preformed epitopes as soon as the redox potential is raised. By forming the correct disulfide bridges, the native-like three-dimensional fold (i.e. the native conformation or structure) of the mature rubella E1 antigen is essentially restored in a locally confined area so that anti-rubella antibodies are capable of recognizing and binding to the rubella E1 antigen variants according to the invention. For example, a rubella E1 (201-432) antigen which is expected to form a first disulfide bridge between Cys 225 and Cys 235 (C13-C14) and a second disulfide bridge between Cys 349 and Cys 352 (C17-C18) harbors the cysteine residues at positions 225, 235, 349 and 352. However, its cysteine residues at positions 242 (C15), 287 (C16), 368 (C19) and 401 (C20) are changed to alanine, serine, or other amino acid residues lacking thiol moieties. The substituting amino acid residues are chosen according to steric and chemical requirements: on the one hand, they ought to fit into the local and overall structure of rubella E1 and, on the other hand, they must not interfere with the correct disulfide bonding by forming mixed disulfides leading to misfolded, abortive protein species.

According to the present invention the term disulfide bridge relates to two cysteine residues which are in close vicinity in the three-dimensional structure of a protein and whose thiol moieties can be oxidized to form a covalent disulfide bond. The rate of disulfide-bond formation depends on the proximity of the two cysteine residues, defined as the probability of their sulfur atoms of coming within the distance required for thiol/disulfide exchange. Disulfide bridges, which are also termed disulfide bonds (synonyms are SS bonds and SS bridges, respectively), constitute covalent tertiary contacts and usually contribute to the stabilization of the folded conformation. They do so by restricting the conformational flexibility of an unfolded polypeptide chain, i.e., the contribution of SS bonds to the stability of a protein is entropic rather than enthalpic in nature. The formation of disulfide bonds requires an oxidative environment. Therefore, intracellular proteins barely contain disulfide bridges because intracellular compartments, such as the bacterial cytoplasm or the eucaryotic cytosol, are essentially reductive. However, disulfide bridges occur frequently in secreted or translocated proteins, such as the gp41 and gp36 ectodomains from HIV-1 and HIV-2, respectively, and in the rubella envelope proteins E1 and E2.

Usually, disulfide bonds stabilize the protein conformation, i.e., in proteins they fulfill the task to lock the native-like fold. This enables a sequential refolding technique based on uncoupling of conformational and oxidative refolding. Conformational refolding means the rearrangement of an unordered, unfolded polypeptide chain upon transfer to physiological buffer conditions (=refolding conditions) to adopt a native-like fold. In this native-like fold, the matching cysteine pairs are usually arranged in close proximity and suitable orientation so that they can form disulfide bonds and thus stabilize the pre-existing native-like conformation. The formation of the disulfide bonds, with the consequence that the three-dimensional fold is stabilized in a local or a global sense, is also termed "oxidative refolding". In the present invention, the uncoupling of conformational and oxidative refolding is used to introduce correct disulfide bonds in a defined manner. First, in vitro conformational refolding of the various E1 antigen variants is performed under reducing conditions. Subsequently, oxidative refolding is performed by removing the respective reducing agent, raising the redox potential and thus inducing the spontaneous formation of the favourable (i.e. correct) disulfide bonds. Preferably, this refolding process is carried out under conditions characterized by low effective protein concentrations in order to avoid aggregation reactions. It is well established that low effective protein concentrations during refolding do increase the yield of the respective target protein. A well established technique of protein refolding in vitro is the so-called matrix-coupled refolding. Immobilization of unfolded protein molecules to a solid phase and refolding of the matrix-bound protein ensures low effective concentrations since the protein molecules are isolated (infinitely diluted) and unable to interact with neighboring protein molecules. Thus, unwanted detrimental side reactions such as aggregation of hydrophobic refolding intermediates are efficiently suppressed.

The rubella E1 antigens according to the invention may contain one or more additional amino acids at their N- or C-terminal ends or both. When additional amino acids are added it is important that these additional amino acids do not weaken the antigenic properties of the antigen, i.e., that they do not interfere with the use of the antigen in an immunoassay, for instance by lowering the overall solubility of the antigen. The ability of the antigen of being recognized and bound by anti-rubella antibodies in a sample has to be maintained.

According to EP-A-1780282 it could be shown that recombinantly expressed soluble rubella E1 envelope antigens can be produced that are suitable for use in an immunoassay for the detection of anti-rubella antibodies. These antigens are characterized by lacking at least the C-terminal transmembrane region and the anchor segment as well as at least the amino acids 143 to 164 in the middle part of E1. These antigens contain at least the region spanning the C-terminal disulfide bridges Cys 349-Cys 352 and Cys 368-Cys 401 (C17-C18 and C19-C20) and, optionally in addition, Cys 225-Cys 235 (C13-C14), indicating that even a third disulfide bridge may be advantageous in obtaining a suitable antigen for use in immunoassays.

Surprisingly, it has been found that further soluble antigenic rubella E1 variants comprising amino acids 201 to 432 or amino acids 169 to 432 are obtained by deletion of the transmembrane region and the C-terminal anchor segment, preferably from amino acid residues 453 to 481. According to the invention the rubella E1 antigen comprises a soluble fragment harboring two disulfide bonds. Preferably, essentially two disulfide bonds are formed in the antigen to stabilize an antigenic conformation, which is well suited to be recognized and bound by anti-E1 immunoglobulins and which is thus well suited for detecting anti-E1 immunoglobulins. The E1 segment bearing two disulfide-bridges may span the disulfide bond Cys 225-Cys 235 to Cys 349-Cys 352 (C13-C14 to C17-C18) or the disulfide bond Cys 225-Cys 235 to 368-Cys 401 (C13-C14 to C19-C20) or the disulfide bond Cys 176-Cys 185 to Cys 225-Cys 235 (C11-C12 to C13-C14) or the disulfide bond Cys 176 to Cys 185 to Cys 349-Cys 352 (C11-C12 to C13-C14) or the disulfide bond Cys 176-Cys 185 to Cys 368-Cys 401 (C11-C12 to C19-C20).

Most preferably, the transmembrane region from amino acids 453 to about 468 is also deleted. Within the middle part of rubella E1 at least the amino acid residues 143-164 are also deleted.

These new rubella E1 antigens have shown to be soluble and stable under physiological buffer conditions without addition of detergents, for example in a phosphate buffer system at ambient temperature. They are highly immunoreactive (i.e. they are antigenic) in a serological assay and well-suited for the detection of anti-rubella antibodies in human sera.

According to the invention also variants of the rubella E1 antigens are included. The term "variants" in this context relates to protein essentially similar to said protein. In particular, a variant may be an isoform which shows amino acid substitutions, deletions or insertions compared to the amino acid sequence of the most prevalent protein isoform. Preferably, such an essentially similar protein has a sequence similarity to the most prevalent isoform of the protein of at least 80%, preferably at least 85%, more preferably at least 90%, most preferably at least 95%. The term "variant" also relates to a post-translationally modified protein such as a glycosylated or phosphorylated protein. A variant is also a protein or antigen which has been modified for example by covalent or non-covalent attachment of a label or carrier moiety to the protein or antigen. Possible labels, reporter groups or signaling moieties are radioactive, fluorescent, chemiluminescent, electrochemiluminescent, enzymes or others, e.g., like digoxigenin. These labels are known to a person skilled in the art. Further label variants are solid phase binding groups like, e.g., biotin or biotin derivatives attached to proteins, a detailed description of labels is disclosed further down in this specification.

A "rubella E1 antigen" is a protein containing a rubella E1 amino acid sequence that is suitable for use in an immunological assay. This means that the antigen is capable of binding to or being recognized and bound by antibodies specific for rubella, like, e.g., anti-rubella E1 antibodies present in a sample.

A further aspect of the invention relates to a composition of at least two different rubella E1 antigens. The term "rubella E1 antigen" includes such a composition containing a combination of more than one rubella E1 antigen. In particular, a preferred embodiment of the invention is a composition comprising at least two rubella E1 antigens each of which comprises amino acids 201 to 432 or amino acids 169 to 432 with the proviso that each of said antigens lacks sequences corresponding to amino acids 143 to 164 and 454 to 481 of the native rubella E1 antigen and wherein each of the at least two rubella E1 antigens contains two disulfide bridges in different combinations.

A preferred composition of at least two different rubella E1 antigens comprises an antigen with a disulfide bridge between Cys 176 and Cys 185 (C11-C12) and a second disulfide bridge between Cys 225 and Cys 235 (C13-C14). The other antigen within this composition preferably contains a disulfide bridge between Cys 225 and Cys 235 (C13-C14) and a second disulfide bridge between Cys 349 and Cys 352 (C17-C18). Optionally further antigens may be included in this composition, preferably a third rubella E1 antigen that contains a disulfide bridge between Cys 349 and Cys 352 (C17-C18) and a disulfide bridge between Cys 368 and Cys 401 (C19-C20).

In a preferred embodiment according to the invention, the rubella E1 antigen is produced as a recombinant fusion protein. The term "fusion protein" as used in the present invention, refers to a protein comprising at least one protein part corresponding to a rubella E1 antigen according to the invention and at least one protein part derived from another protein that serves the role of a fusion partner.

Folding and purification of proteins is often facilitated by fusing them covalently with tags or partner proteins that fold robustly by themselves. These fusion modules include maltose binding protein, glutathion S-transferase, thioredoxin, NusA, DsbA and chaperones like FkpA. The use of these fusion modules customarily aims at increasing the soluble expression (i.e. the native-like folding) of the respective target protein either in the cytosol or the periplasm of the overproducing *E. coli* host. Preferably chaperones, more preferably chaperones of the peptidyl prolyl isomerase class, most preferably chaperones from the FKBP family of peptidyl proly isomerases are used as fusion proteins within the rubella E1 fusion polypeptide.

Chaperones, which are known as classical "folding helpers", are proteins that assist the folding and maintenance of structural integrity of other proteins. They possess the ability to promote the folding of a protein both in vivo and in vitro. Generally, folding helpers are subdivided into folding catalysts and chaperones. Folding catalysts accelerate the rate limiting steps in protein folding due to their catalytic function. Chaperones are known to bind to denatured or partially denatured proteins and thus help to renature or, alternatively, degrade proteins. Thus, unlike folding catalysts, chaperones exert a mere binding function. Examples of catalysts and chaperones are described in detail in WO 03/000877.

To date, several distinct families of chaperones are known. All these chaperones are characterized by their ability to bind unfolded or partially unfolded proteins and have a physiological function that is linked to the correct folding of proteins or the degradation and removal of denatured or aggregated protein. It has been demonstrated that an enhanced expression of chaperones may facilitate the recombinant production of a protein. It is also known that an increased production of proteins can be achieved by using a gene construct encoding both the target protein sequence and a chaperone sequence. In all these applications of chaperones as tools in biotechnology the major obstacle is to find an appropriate and functional chaperone for a given target molecule. Since many chaperones exhibit a narrow substrate specificity and work in an energy-dependent mode, the search for an appropriate (i.e. solubilizing) binding partner for a given target protein is far from trivial. Briefly, the approach to use chaperones for increased production yields of native-like folded proteins is mainly based on the binding and thus solubilizing function of chaperone proteins. After recombinant production of a fusion protein comprising chaperone and target protein, the chaperone moiety is customarily cleaved off from the resulting fusion polypeptide to yield the desired protein in pure form.

According to the present invention the recombinantly produced fusion protein containing a fusion module and a rubella E1 antigen can be readily obtained from inclusion bodies in a soluble and functional form. Moreover, the disclosed rubella E1 protein is part of a fusion protein, it shows a high solubility at physiological buffer conditions and can readily be obtained in a native-like and immunoreactive (i.e. antigenic) structure or conformation.

The rubella E1 fusion protein according to the present invention is very easy to handle. In other words, it is easy to renature such a fusion protein with high yields following a robust and simple refolding protocol. The denaturant-unfolded unstructured polypeptide can be refolded in different ways, all resulting in a thermodynamically stable and soluble native-like form that is antigenic. Refolding is achieved at high yields, both by dialysis and by rapid dilution, as well as by renaturing size exclusion chromatography or matrix-assisted refolding. Preferably, refolding techniques enabling very low effective protein concentrations during renaturation are employed, such as renaturing size exclusion chromatography or matrix-assisted refolding. Refolding techniques such as dialysis or rapid dilution are successful as well, given the protein concentrations are kept low during the refolding process.

Preferably, a soluble protein according to the present invention is produced by fusing a rubella E1 antigen to a chaperone from the class of peptidyl-prolyl-isomerases. Therefore, a preferred embodiment according to the invention relates to the fusion of a rubella E1 antigen with a peptidyl-prolyl-isomerase class chaperone, preferably with an FKBP chaperone and most preferably with a SlyD or FkpA chaperone.

Recombinant production methods aside, the rubella E1 antigens according to the invention can also be produced by chemical synthesis, whereby the synthesis can be carried out in homogeneous solution or in solid phase as known in the art.

The above described rubella E1 antigens can be optimized according to the requirements of a specific immunoassay for the detection of anti-rubella antibodies. For example the antigens can be brought into a defined monomeric or oligomeric state. In an oligomeric form the antigens are suitable for use in an immunological assay for the detection of IgM antibodies in a human sample. The E1 fusion polypeptides according to the invention may be polymerized, e.g., by chemical cross-linking resulting in an antigen that is preferably recognized and bound by IgM antibodies. In a further preferred embodiment of the present invention a mixed polymer may be obtained composed of rubella proteins E1, E2 and Core protein C. Rubella E2 and Core proteins are immunodominant rubella antigens well known in the art.

The rubella E1 protein according to the invention can also be prepared by means of recombinant DNA techniques. The term "recombinant DNA molecule" refers to a molecule which is made by the combination of two otherwise separated segments of sequence accomplished by the artificial manipulation of isolated segments of polynucleotides by genetic engineering techniques or by chemical synthesis. In doing so one may join together polynucleotide segments of desired functions to generate a desired combination of functions.

Large amounts of the polynucleotides may be produced by replication in a suitable host cell. Natural or synthetic DNA fragments coding for proteins or fragments thereof will be incorporated into recombinant polynucleotide constructs, typically DNA constructs, capable of introduction into and replication in a prokaryotic or lower or higher eukaryotic cell such as described by Sambrook et al., (1989, Molecular Cloning: A Laboratory Manual).

The term lower eukaryotes refers to host cells such as yeast, fungi and the like. Lower eukaryotes are generally but not necessarily unicellular. The term "prokaryotes" refers to hosts such as *E. coli, Lactobacillus, Lactococcus, Salmonella, Streptococcus, Bacillus subtillis* or *Streptomyces*. Also these hosts are contemplated within the present invention. Preferred lower eukaryotes are yeast's, particularly species within *Schizosaccharomyces, Saccharomyces, Kluiveromyces, Pichia* (e.g. *Pichia pastoris*), *Hansenula* (e.g. *Hansenula polymorpha*), *Schwaniomyces, Schizosaccharomyces, Yarowia, Zygosaccharomyces* and the like. *Saccharomyces cerevisiae* and *S. carlsbergensis* are the most commonly used yeast hosts, and are convenient fungal hosts. The term "higher eukaryotes" refers to host cells derived from animals, such as mammals, reptiles, insects, and the like. Presently preferred higher eukaryote host cells are derived from Chinese hamster (e.g. CHO), monkey (e.g. COS and Vero cells), baby hamster kidney cells (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like.

A further subject matter of the present invention relates to a recombinant DNA molecule, encoding a rubella E1 antigen, comprising at least one nucleotide sequence coding for a rubella E1 antigen spanning a region that contains two disulfide bridges as described below. A preferred subject of the invention is a recombinant DNA molecule, encoding a rubella E1 antigen, comprising at least one nucleotide sequence coding for a rubella E1 antigen wherein upstream thereto is at least one nucleotide sequence coding for a a peptidyl-prolyl-isomerase class chaperone, preferably for an FKBP chaperone. This recombinant DNA molecule according to the invention encodes a rubella E1 antigen comprising amino acids 201 to 432 with the proviso that said antigen lacks sequences corresponding to amino acids 143 to 164 and 454 to 481 of the mature rubella E1 antigen wherein a) one disulfide bridge is formed between Cys 225 and Cys 235 and a second disulfide bridge is formed between Cys 349 and Cys 352 or
b) one disulfide bridge is formed between Cys 225 and Cys 235 and a second disulfide bridge is formed between Cys 368 and Cys 401.

Also contemplated is a recombinant DNA molecule encoding a rubella E1 antigen, comprising at least one nucleotide sequence coding for a rubella E1 antigen wherein upstream thereto is at least one nucleotide sequence coding for a peptidyl-prolyl-isomerase class chaperone, preferably for an FKBP chaperone. In this recombinant DNA molecule the nucleic acid sequence encoding the rubella E1 antigen comprises amino acids 169 to 432 with the proviso that said antigen lacks sequences corresponding to amino acids 143 to 164 and 454 to 481 of the native rubella E1 antigen wherein a) one disulfide bridge is formed between Cys 176 and Cys 185 and a second disulfide bridge is formed between Cys 225 and Cys 235 or
b) one disulfide bridge is formed between Cys 176 and Cys 185 and a second disulfide bridge is formed between Cys 349 and Cys 352 or
c) one disulfide bridge is formed between Cys 176 and Cys 185 and a second disulfide bridge is formed between Cys 368 and Cys 401.

Prolyl isomerases may comprise different subunits or modules of different function, e.g., a module exhibiting catalytic activity and a module exhibiting the chaperone or binding activity. Such modular members of the FKBP family are FkpA, SlyD and trigger factor. In a preferred embodiment the invention relates to a recombinant DNA molecule, characterized in that the nucleic acid encoding the FKBP chaperone is selected from the group consisting of FkpA, SlyD and trigger factor.

It is not always necessary to use the complete sequence of a molecular chaperone. Functional fragments of chaperones (so-called modules) which still possess the required structures, functions and stabilities may also be used (cf. WO 98/13496).

The FkpA variant used as expression tool according to the present invention lacks its N-terminal signal sequence. A close relative of FkpA, namely SlyD, consists of a structured N-terminal domain responsible for catalytic and chaperone functions and of a largely unstructured C-terminus that is exceptionally rich in histidine and cysteine residues. WO 03/000878 discloses that a C-terminally truncated variant of SlyD comprising amino acids 1-165 exerts exceptionally positive effects on the efficient expression and overproduction of target proteins. Unlike in the wild-type SlyD (which harbors six reactive cysteine residues in a presumably unstructured environment), the danger of detrimental disulfide shuffling leading to falsely connected, abortive and aggregation-prone protein species is successfully circumvented in the truncated SlyD-variant (1-165*) as disclosed in WO 03/000878. A recombinant DNA molecule comprising a rubella E1 antigen having a region spanning the two disulfide bridges as described above and a truncated SlyD (1-165*) represents a preferred embodiment of the present invention. A further preferred embodiment is the use of tandem SlyD chaperones. Preferably, two tandem SlyD (1-165*) chaperones are fused to the N-terminal end of rubella E1 (see also Example 1).

In a preferred mode of designing a rubella E1 antigen according to the present invention no signal peptides of possibly periplasmic fusion partners are included. The expression systems according to the present invention have been found most advantageous when working as cytosolic expression system. The more efficient this cytosolic expression is, the more inevitable is the accumulation of the target fusion polypeptide in insoluble and inactive inclusion bodies. Customarily, expression and overproduction strategies aim at soluble production in the bacterial cytosol by preventing inclusion body formation. The approach taken according to the invention is quite different in so far as a massive cytosolic overproduction is favored, followed by a renaturation protocol facilitating high yields of native-like folded (i.e. well-structured, native-like folded) antigenic protein. A high amount of rubella E1 antigen is produced and accumulates in inclusion bodies, but the recombinant rubella E1 proteins according to the present invention are very easy to handle, e.g., easy to solubilize and to refold into a functional (i.e. antigenic) conformation.

Preferably the recombinant DNA molecule of the present invention is further characterized in that it comprises at least one nucleotide sequence coding for a peptidic linker of 10-100 amino acids located in between said sequence coding for a rubella E1 antigen and said sequence coding for an FKBP chaperone. As known in the art such linker polypeptide is designed as most appropriate for the intended application, especially in terms of length, flexibility, charge, and hydrophilicity. Furthermore, such DNA sequence coding for a linker may a proteolytic cleavage site for the expressed protein. Such DNA sequence may also serve as a polylinker, i.e., it may provide multiple DNA restriction sites to facilitate fusion of the DNA fragments coding for a rubella E1 antigen and a chaperone domain. After expression and purification of the obtained fusion protein and subsequent refolding into a soluble and immunoreactive conformation the polylinker may as well facilitate the release of the rubella E1 protein from the fusion protein complex.

A soluble rubella E1 antigen and variants of this protein according to the present invention may be precisely excised out of the fusion construct thus yielding the sole rubella E1 antigen comprising amino acids 201 to 432 or 169 to 432 and characterized by lacking at least the C-terminal transmembrane region and the anchor segment (amino acids 453 to 481) as well as at least the segment from amino acids 143 to 164 in the middle part of the molecule. The antigen further contains a region spanning two disulfide bonds, i.e., the region from the disulfide bond Cys 225-Cys 235 to Cys 349-Cys 352 or the region from the disulfide bond Cys 225-Cys 235 to 368-Cys 401 or the region from the disulfide bond Cys 176-Cys 185 to Cys 225-Cys 235 or the region from the disulfide bond Cys 176-Cys 185 to Cys 349-Cys 352 or the region from the disulfide bond Cys 176-Cys 185 to Cys 368-Cys 401.

A further subject matter of the invention relates to a recombinant DNA which comprises a single nucleotide sequence coding for an FKBP chaperone and a single nucleotide sequence coding for a rubella E1 protein.

A fusion protein comprising at least two FKBP chaperone domains and one target protein or target antigen domain is also very advantageous. In a further preferred embodiment the recombinant DNA molecule according to the present invention comprises two sequences coding for a FKBP chaperone and one sequence coding for a rubella E1 protein. The fusion of two FKPB chaperone domains imparts an improved solubility to the rubella E1 protein.

The term "at least two" is used to indicate that two or more nucleotide sequences coding for a FKBP chaperone domain may be used in construction of a recombinant DNA molecule without departing from the scope of the present invention. Preferably, the rubella E1 chaperone fusion protein will contain at least two and at most four sequences coding for a chaperone.

The DNA molecule may be designed to comprise both the DNA sequences coding for the FKBP chaperone upstream to the target protein. Alternatively the two FKBP domains may be arranged to sandwich the target protein. A recombinant DNA molecule comprising both FKBP domains upstream to the sequence coding for a rubella E1 antigen represents a preferred embodiment according to the present invention. In order to increase the genetic stability of the expression system and to circumvent homologous recombination in the host cell, different nucleotide sequences may be used to encode identical chaperone moieties fused to the target molecule. Put simply, the coding sequences for all repetitive elements in the protein structure (such as tandem chaperone fusions or repetitive linker segments and the like) should be varied, whereby the codon usage of the respective host system should be taken into account. This is easily accomplished by exploiting the degeneracy of the genetic code which is well-known to any skilled person in the field of protein technology.

In an alternative embodiment of the invention the recombinant DNA molecule is characterized in that one sequence coding for a peptidyl prolyl isomerase chaperone is located upstream of a rubella E1 antigen and the other sequence coding for a peptidyl prolyl isomerase chaperone is located downstream of the sequence coding for a rubella E1 antigen.

The DNA construct comprising two chaperone domains as well as a sequence coding for a rubella E1 antigen preferably also contains two linker peptides of 10 to 100 amino acids in between these domains. In order to allow for a systematic cloning the nucleotide sequences coding for these two linker peptide sequences preferably are different. This difference in nucleotide sequence does not necessarily result in a difference in the amino acid sequence of the linker peptides.

In cases where it is desired to release one or all of the chaperones out of a fusion protein according to the present invention the linker peptide is constructed to harbor a proteolytic cleavage site. As described above, the proteolytic cleavage site may also serve as a polylinker, i.e., it may provide multiple DNA restriction sites to facilitate fusion of the DNA fragments coding for a rubella E1 protein and a chaperone domain. A recombinant DNA molecule encoding a fusion protein comprising at least one polypeptide sequence coding for a rubella E1 antigen, upstream thereto at least one nucleotide sequence coding for a FKBP chaperone selected from the group consisting of FkpA, SlyD, and trigger factor and additionally comprising a nucleic acid sequence coding for a peptidic linker comprising a proteolytic cleavage site, represents a further embodiment of this invention.

A further aspect of the invention is an expression vector comprising operably linked a recombinant DNA molecule according to the present invention, i.e., a recombinant DNA molecule encoding a fusion protein comprising at least one polynucleotide sequence coding for a rubella E1 antigen and upstream thereto at least one nucleotide sequence coding for a peptidyl prolyl isomerase chaperone, preferably an FKBP chaperone, wherein the FKBP chaperone is selected from FkpA, SlyD, and trigger factor, has proven to be very advantageous.

The expression vector comprising a recombinant DNA according to the present invention may be used to express the fusion protein in a cell free translation system or may be used to transform a host cell. In a preferred embodiment the present invention relates to a host cell transformed with an expression vector according to the present invention.

Expression and cloning vectors will likely contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and grow under selective conditions. Typical selection genes include but are not limited to those encoding proteins that (a) confer resistance to antibiotics or other toxic substances, e.g., ampicillin, tetracycline, etc.; (b) complement auxotrophic deficiencies; or (c) supply critical nutrients not available from complex media. The choice of the proper selectable marker will depend on the host cell, and appropriate markers for different hosts are known in the art.

The vectors containing the rubella E1 antigen of interest can be introduced into the host cell by any method known in the art. These methods vary depending upon the type of cellular host, including but not limited to transfection employing calcium chloride, rubidium chloride, calcium phosphate, DEAE-dextran, other substances, and infection by viruses. Large quantities of the rubella E1 protein of the present invention may be prepared by expressing the polypeptides of the present invention by means of vectors or other expression vehicles in compatible host cells.

Construction of a vector according to the present invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

The invention also concerns a host cell transformed with said expression vector.

Also contemplated is a method for producing a soluble and immunoreactive rubella E1 antigen, preferably as a fusion protein containing the E1 antigen and a peptidyl prolyl isomerase class chaperone. Preferably, the peptidyl prolyl isomerase is an FKBP chaperone, more preferably an FKBP chaperone selected from the group consisting of SlyD, FkpA and trigger factor.

This method comprises the steps of a) culturing host cells transformed with the above-described expression vector containing a gene encoding a fusion protein comprising a rubella E1 antigen and a peptidyl prolyl isomerase class chaperone or a functional fragment thereof, which still possesses the chaperoning binding activity
b) expression of the gene encoding said fusion protein
c) purification of said fusion protein
d) refolding into a soluble and immunoreactive (i.e. antigenic) conformation.

The present invention discloses a method for the detection of anti-rubella antibodies in an isolated human sample wherein the rubella E1 antigen is used as a binding partner for the antibodies. The invention thus concerns a method for the detection of antibodies specific for rubella in an isolated sample, said method comprising a) forming an immunoreaction admixture by admixing a body fluid sample with a rubella E1 antigen according to the invention
b) maintaining said immunoreaction admixture for a time period sufficient for allowing antibodies against said rubella E1 antigen present in the body fluid sample to immunoreact with said rubella E1 antigen to form an immunoreaction product; and
c) detecting the presence of any of said immunoreaction product.

A further subject matter of the present invention is a method for the detection, determination and quantification of anti-rubella antibodies of the subclasses IgG or IgM or both in a sample wherein the rubella E1 antigen is used as a capture reagent or binding partner or both for the antibodies. All biological liquids known to the expert can be used as samples for the detection of anti-rubella antibodies. The samples preferred are body liquids like whole blood, blood sera, blood plasma, urine, saliva, etc.

With respect to diagnostic procedures, clear advantages of a soluble rubella E1 antigen-fusion protein, more preferably a soluble rubella E1 antigen-chaperone fusion protein according to the present invention are, e.g., the increased solubility and stability of the rubella E1 protein under physiological buffer conditions and the concomitant constancy of the diagnostic sensitivity, the increased number of accessible native-like conformational epitopes, the possibility to easily label a correctly folded rubella E1 antigen and the lot-to-lot consistency in the manufacturing process.

The detection of specific antibodies of a certain immunoglobulin class can be performed by capturing the immunoglobulin to a solid phase to which a specific antigen has been immobilized. The captured immunoglobulin is subsequently detected by a labelled antibody specific for human immunoglobulins of a certain class. Yet, this indirect assay format can only be carried out in a two step setup allowing a washing step which eliminates unspecific immunoglobulins prior to detection. A one-step assay format, which is frequently realized in automatic immunoassay analyzers, requires the direct assay format of a double antigen sandwich, i.e., the specific antibody forms an immunocomplex binding to a first antigen which is immobilized to a solid phase or will mediate immobilization to a solid phase and to a second antigen carrying a label thus allowing quantitative or qualitative detection of the specifically bound antibody analyte. The selective determination of specific IgG antibodies in the presence of IgM antibodies of the same specificity in a one-step double antigen sandwich format strictly requires the use of soluble, monomeric or defined oligomeric antigens as described for example in European Patent application EP 0 944 838.

Well-known labels are marker groups or effector groups, like solid phase binding groups. A labeled soluble rubella E1 antigen-fusion protein, more preferably a labeled soluble rubella E1 antigen-chaperone protein represents a further preferred embodiment according to the present invention.

The labeling group can be selected from any known signaling moiety groups, such as dyes, luminescent labeling groups such as chemiluminescent groups, e.g., acridinium esters or dioxetanes, or fluorescent dyes, e.g., fluorescein, coumarin, rhodamine, oxazine, resorufine, cyanine and derivatives thereof. Other examples of signaling moieties or marker groups are luminescent metal complexes, such as ruthenium or europium complexes, enzymes, e.g., as used for ELISA or for CEDIA (Cloned Enzyme Donor Immunoassay, e.g., EP-A-0 061 888), and radioisotopes.

Effector groups comprise, for example, one partner of a bioaffine binding pair. While performing an assay, the effector group interacts specifically and preferably non-covalently with the other partner of the bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred binding pair members comprise hapten, antigen and hormone. Especially preferred are haptens like digoxin and biotin and analogs thereof.

Preferably, the soluble complex comprising a rubella E1 antigen and a prolyl peptidyl isomerase chaperone is used in an immunoassay for detection of anti-rubella antibodies, i.e., antibodies specific for rubella. In a further preferred embodiment, a labeled soluble complex comprising a rubella E1 antigen and a prolyl peptidyl isomerase chaperone is used in an immunoassay for detection of antibodies to rubella. Most preferred, the labeled complex is an intramolecular complex within a recombinant polypeptide comprising the chaperone and a rubella E1 antigen.

Immunoassays are well known to the skilled artisan as well as are methods for carrying out such assays and practical applications and procedures. The novel soluble rubella E1 antigen-fusion protein, more preferably the novel soluble rubella E1 antigen chaperone fusion polypeptide can be used to improve assays for the detection of anti-rubella antibodies independently of the mode of detection (e.g., radioisotope assay, enzyme immunoassay, electrochemiluminescence assay, etc.) or the assay principle (e.g., test strip assay, sandwich assay, or homogenous assay, etc.).

For the reliable and sensitive detection of an rubella infection, it is essential to measure anti-viral antibody in bodily fluid samples. The soluble complex according to the present invention enables the detection of anti-rubella antibodies at physiological buffer conditions, i.e., without the need to include detergents that keep the antigen in a soluble form. The detection of anti-rubella antibodies is an imperative part of such combined rubella detection systems. In a preferred embodiment, the present invention therefore relates to rubella detection systems comprising the detection of anti-rubella antibodies based on the use of a rubella E1 antigen-fusion protein, more preferably the use of a rubella E1 antigen chaperone protein.

As known from the art, antibodies to infectious agents such as bacteria, fungi or viruses, are preferably detected by an assay performed according to the double antigen sandwich format (sometimes this assay format is also termed double antigen bridge format, because the two antigens are bridged by the antibody analyte). In such an assay the ability of an antibody to bind at least two different molecules of a given antigen with its two (IgG, IgE), four (IgA) or 10 (IgM) paratopes is required and used.

Detection of antibodies from bodily fluids according to the bridge concept can be performed in many different assay setups. A simple setup comprises the direct coating of an antigen to a solid phase and the use of the same antigen in a labeled form for the signal generation. Under appropriate assay conditions, a specific antibody analyte in a sample forms a bridge between the solid phase bound antigen and the labeled antigen. Therefore, only if the investigated antibody is present in the sample, a bridge is formed and a signal can be detected.

The basic structures of "solid phase antigen" and the "detection antigen" preferably are the same. For example, a protein comprising one or several epitopes (i.e. an antigen) may be used directly or indirectly coated to a solid phase. The same antigen, bound to a label or marker is used as detection antigen. It is also possible to use similar and immunologically cross-reactive but different rubella E1 antigens in a double antigen bridge assay. The essential requirement for performing such assays is that the relevant epitope or the relevant epitopes are present on both antigens. It is self-evident that there are many variants of the double antigen bridge assay format. Such variants comprise, for example, the indirect coating of an rubella E1 antigen to a solid phase. Preferably, a specific binding pair, most preferably the biotin-streptavidin (or -avidin) system, is used to indirectly immobilize an rubella antigen to a solid phase. On the other hand, the rubella E1 antigen used for detection in such a system may not directly carry a marker (e.g., a radioisotope, enzyme, fluorescent molecule, etc.), but rather may be indirectly detectable by, e.g., carrying a hapten (for example, digoxin). Such indirect detection then, e.g., may be performed by a labeled anti-digoxin antibody.

A preferred embodiment of the present invention is therefore an immunoassay according to the double antigen bridge concept wherein a first rubella E1 antigen according to the present invention, and a second rubella E1 antigen according to the present invention is used.

In more detail, an immunoassay for the determination of anti-rubella antibodies according to the double antigen bridge format is carried out by incubating a sample containing the anti-rubella antibodies with two different rubella E1 antigens, i.e., a first and a second rubella E1 antigen, wherein each of the said antigens binds specifically to said anti-rubella antibodies. The first antigen can be bound directly or indirectly to a solid phase and preferably carries an effector group such as, e.g., biotin, which is part of a bioaffine binding pair. The second antigen carries a label or signaling moiety. Thus an immunoreaction admixture is formed. A solid phase to which the first antigen can be immobilized is added either prior to the addition of the sample to said antigens or, preferably, after the immunoreaction admixture is formed. This immunoreaction admixture is maintained for a time period sufficient for allowing anti-rubella antibodies against said rubella E1 antigens in the body fluid sample to immunoreact with said rubella E1 antigens to form an immunoreaction product. In the subsequent separation step the liquid phase is separated from the solid phase. Finally, the presence of any of said immunoreaction products is detected in the solid or liquid phase or both.

In a further preferred embodiment, the present invention relates to an immunoassay according to the double antigen bridge concept characterized in that a first rubella E1 antigen-fusion protein complex is used as capture antigen and a second rubella E1 antigen-fusion protein complex is used as detection antigen.

The rubella E1 antigen-fusion protein complex, preferably the rubella E1 antigen-chaperone complex as disclosed in the present invention does not only bring about an improved solubility of various proteins that are otherwise difficult to handle (such as rubella E1), but they also facilitate an immunoassay according to the double antigen bridge concept in an advantageous manner.

It is an especially attractive feature of such an immunoassay according to the double antigen bridge concept, that it is now possible to use different but functionally equivalent chaperones for complex formation with the solid phase bound antigen and for complex formation with the detection antigen, respectively. Such modification of an assay further reduces the omnipresent problem of non-specific binding due to immunological cross-reactivities. Antibodies in a sample, which are reactive to a chaperone and thus might evoke a false positive signal, will be hindered to form a bridge as soon as different chaperones are used to solubilize the solid phase antigen and the detection antigen, respectively.

Therefore, in this mode of the invention, the likelihood of a positive signal due to non-specific binding is largely reduced. In a preferred embodiment, the present invention therefore relates to an immunoassay according to the double antigen bridge concept which is characterized in that the first chaperone and the second chaperone of a first and a second chaperone-rubella E1 antigen complex differ from each other. Preferably, the first and the second chaperone originate from different FKBP chaperones. In a preferred embodiment of the present invention a SlyD-E1 fusion protein on one side and a FkpA-E1 fusion protein on the other side is used in a double antigen sandwich immunoassay. Preferred FKBP chaperones originate from *Escherichia coli, Treponema pallidum, Pasteurella multocida, Vibrio cholerae, Yersinia pestis, Therms thermophilus* and *Thermococcus* sp.

Immunological cross-reactions via the chaperone parts of two fusion polypeptides in a double antigen sandwich format clearly would evoke false positive signals and thereby compromise the specificity of an immunoassay. The use of two functionally equivalent but different chaperones as fusion partners on both sides of the bridge format may reduce this omnipresent danger of cross-reactivity in immunoassays. "Different chaperones" may mean the strategy of using homologous (i.e. related) chaperones from different organisms as well as different chaperones from the same organism. Yet, in addition to using different chaperone fusion partners for the antigens employed on both sides of a double antigen sandwich assay, all moieties and neoepitopes which are not part of the actual antigen should be represented in a soluble polymerized anti-interference component which is added to the assay in sufficient amounts. An anti-interference substance could, for instance, comprise a tandem SlyD molecule including any linker, spacer and tag sequences that are also part of the chaperone-antigen polypeptide. It can even comprise the labeling moiety in an inactive form, i.e., it can comprise a labeling moiety mimic without quenching true positive signals.

The same holds true for the binding moiety that mediates immobilization to the solid phase: A mimic of this binding moiety which is no longer binding-competent due to chemical modifications may also be envisaged in the design of an anti-interference substance. This anti-interference substance could then be polymerized by means of chemical crosslinkers and, as a soluble polymer, be added to the reaction mixture in order to capture immunoglobulins of any type directed against any moiety of the antigen polypeptide which is not part of the genuine viral protein used for antibody detection, for example the rubella E1 protein in rubella immunodiagnostics. The high epitope density of the chemically polymerized anti-interference substance would ensure efficient binding and elimination of IgM molecules which are reactive to, e.g., chaperone, linker, spacer or label epitopes and thus are a frequent cause of interferences in immunoassays.

Most of the chaperones that are best characterized have been isolated from *Escherichia coli*, which is widely used in biotechnological research. Since *Escherichia coli* is a widely distributed bacterial species, many mammals have developed antibodies against proteins derived from this bacterium. As described above, in order to reduce the likelihood of false positive reactions caused by such antibodies, it is preferred to use a prolyl peptidyl isomerase chaperone pair derived from distinct bacterial species, for instance one chaperone from a mesophilic and one chaperone from a thermophilic organism. In a further preferred embodiment the chaperone is derived from extremophilic bacteria, especially of the group of bacteria comprising *Thermatoga maritima, Aquifex aeolicus, Thermococcus* sp., *Methanococcus thermolithotrophicus, Methanococcus jannaschii, Pyrococcus Horikoshii, Aeropyrum pernix* and *Thermus thermophilus*.

The use of a chaperone-antigen complex in an immunoassay in general, and preferably in an immunoassay according to the bridge concept, also provides the possibility to specifically derivatise the chaperone of such a complex without modification of the antigen itself. It is obvious that the modification of a protein by any chemical moiety, for example, the coupling of a label to that molecule, poses the risk of negatively influencing the polypeptide. For example, the epitope under investigation may be altered and thus compromised, or non-specific binding may be favored by such labeling, or neoepitopes may be generated interfering with the specificity of an immunoassay. According to the present invention, it is now possible to derivatise specifically the chaperone within a rubella E1 antigen-chaperone complex.

In a preferred embodiment, an immunoassay according to the double antigen bridge concept is further characterized in that the first rubella E1 antigen-chaperone complex used as capture antigen comprises a solid phase binding group.

In a further preferred embodiment, an immunoassay according to the bridge concept is performed, which is further characterized in that the second rubella E1 antigen-chaperone complex used as detection antigen comprises a marker group or signaling moiety.

The present invention further relates to the use of at least one antigen of rubella E1 which contains two disulfide bridges in a diagnostic test for the detection of anti-rubella antibodies. The invention also relates to the use of a composition comprising at least two different rubella E1 antigens, each of which contains two disulfide bridges, in a diagnostic test for the detection of anti-rubella antibodies. The disclosed uses and assays comprise the addition of further common additives as required and well-known in the art.

A further subject matter of the invention is a reagent kit for the detection of antibodies against rubella, which contains at least one of the rubella E1 antigens suitable for specifically binding to rubella antibodies to be determined and possibly carries a label. The kit may contain other usual additives if necessary. In particular the reagent kit contains a rubella E1 antigen comprising amino acids 201 to 432 with the proviso that said antigen lacks sequences corresponding to amino acids 143 to 164 and 454 to 481 of the native rubella E1 antigen and contains two disulfide bridges wherein a) one disulfide bridge is formed between Cys 225 and Cys 235 and a second disulfide bridge is formed between Cys 349 and Cys 352 or
b) one disulfide bridge is formed between Cys 225 and Cys 235 and a second disulfide bridge is formed between Cys 368 and Cys 401, wherein antigen a) is most preferred.

In a further preferred reagent kit at least one rubella E1 antigen is contained that comprises amino acids 169 to 432 with the proviso that said antigen lacks sequences corresponding to amino acids 143 to 164 and 454 to 481 of the native rubella E1 antigen and contains two disulfide bridges wherein a) one disulfide bridge is formed between Cys 176 and Cys 185 and a second disulfide bridge is formed between Cys 225 and Cys 235 or
b) one disulfide bridge is formed between Cys 176 and Cys 185 and a second disulfide bridge is formed between Cys 349 and Cys 352 or
c) one disulfide bridge is formed between Cys 176 and Cys 185 and a second disulfide bridge is formed between Cys 368 and Cys 401.

In yet another embodiment of the invention the reagent kit contains a composition comprising at least two different rubella E1 antigens each of which comprises amino acids 201 to 432 or 169 to 432 with the proviso that each of said antigens lacks sequences corresponding to amino acids 143 to 164 and 454 to 481 of the native rubella E1 antigen and wherein each of the at least two rubella E1 antigens contains two disulfide bridges.

In addition, each of the reagent kits disclosed above contains control and standard solutions as well as reagents in one or more solutions with the common additives, buffers, salts, detergents et cetera as used by the person skilled in the art.

A further embodiment is the use of the rubella E1 antigens according to the invention as vaccines. The preparation of vaccines which contain an immunogenic polypeptide as active ingredient is known in the art. Such vaccines are commonly prepared as injectables, either as liquid solutions or suspensions. The active ingredient, i.e., the rubella E1 antigen or its fusion protein is mixed with excipients which are pharmaceutically acceptable and compatible with the active ingredient like, e.g., water, aqueous physiological buffers, saline, dextrose, glycerol, ethanol. The vaccines are conventionally administered by injection.

The Examples section illustrates the invention.

EXAMPLE 1

Construction of an Expression Plasmid Comprising Tandem-EcSlyD and the Rubella E1 Ectodomain Fragment E1 (201-432) and (169-432)

The sequence of the E1 precursor protein from rubella strain Therien (Dominguez et al. 1990, Virology 177, 225-238) was retrieved from the SwissProt database (acc. no. P07566). A synthetic gene encoding rubella E1 (aa 1-432) was purchased from Medigenomix (Martinsried, Germany).

The rubella E1 ectodomain contains 20 cysteines. This disulfide complexity is a major obstacle for simple recombinant production of the rubella E1 ectodomain in prokaryotic hosts such as *E. coli.* 20 cysteine residues within the ectodomain dramatically increase the likelihood of disulfide mispairing, which usually leads to misfolded and aggregation-prone protein conformations. To reduce the disulfide complexity, a variant, in which all cysteine residues were mutated to alanine or serine was used. Starting with this disulfide-free E1 variant, two large soluble and monomeric E1 variants were obtained, the rubella E1 fragments 201-432 and 169-432, respectively. After that, disulfide pairs were introduced, first individually and then in combinations of two or three, into the E1 fragments. To this end, only the cysteines necessary for disulfide formation were introduced by site-directed mutagenesis, whereas all the other cysteine residues still remained mutated to alanine. QuikChange (Stratagene, La Jolla, Calif., USA) and standard PCR techniques were used to generate point mutations, deletion and extension variants, or restriction sites in the respective expression cassettes. On the basis of the pET24a expression plasmid of Novagen (Madison, Wis., USA) the following cloning steps were performed. The vector was digested with NdeI and XhoI and a semi-synthetic cassette comprising tandem-SlyD and the rubella E1 fragment 201-432 or 169-432, respectively, was inserted. All recombinant E1 fusion polypeptide variants contained a C-terminal hexahistidine tag to facilitate Ni-NTA-assisted purification and refolding.

Figure 5:
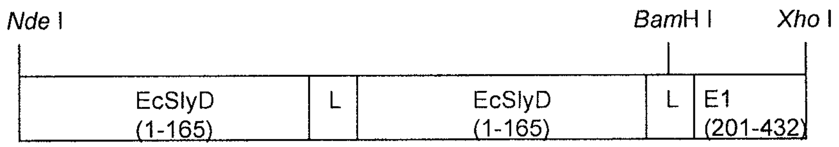
FIG. 5 shows a scheme of the resulting rubella E1 antigen 201-432 having two tandem SlyD chaperones fused to its N-terminal end. $(GGGS)_5GGG$ disclosed as SEQ ID NO: 13.

FIG. 5 shows a scheme of the resulting rubella E1 antigen 201-432 having two tandem SlyD chaperones fused to its N-terminal end. $(GGGS)_5GGG$ disclosed as SEQ ID NO: 13.

The insert of the resulting plasmid was sequenced and found to encode the desired fusion protein. The amino acid sequences of the inserted rubella E1 antigens are shown in the sequence listing of the present invention.

Using this strategy the following rubella E1 antigens, with a tandem SlyD part fused to their N-terminal ends were obtained as follows:

No disulfide bridge (as a reference E1 variant lacking any cysteine residues)

E1 169-432 as shown in SEQ ID NO: 2

E1 201-432 as shown in SEQ ID NO: 1.

SEQ ID NOs. 1 (201-432) and 2 (169-432) exhibit the amino acid sequence of rubella E1 (strain Therien) as accessible in Swiss Prot data base ID P07566.

Single Disulfide Bridges:

E1 169-432 (C11-C12), E1 201-432 (C13-C14), E1 201-432 (C17-C18), E1 201-432 (C19-C20)

Double Disulfide Bridges:

E1 201-432 (C17-C18, C19-C20) as shown in SEQ ID NO: 3

E1 201-432 (C13-C14, C17-C18) as shown in SEQ ID NO: 4

E1 201-432 (C13-C14, C19-C20) as shown in SEQ ID NO: 5

E1 169-432 (C11-C12, C13-C14) as shown in SEQ ID NO: 6

E1 169-432 (C11-C12, C17-C18) as shown in SEQ ID NO: 7

E1 169-432 (C11-C12, C19-C20) as shown in SEQ ID NO: 8

Triple Disulfide Bridges:

E1 201-432 (C13-C14, C17-C18, C19-C20) as shown in SEQ ID NO: 11

E1 169-432 (C11-C12, C17-C18, C19-C20) as shown in SEQ ID NO: 9

The experimental results for the immunological reactivity of these rubella E1 antigens in an immunoassay for the detection of anti-rubella antibodies as described in Examples 6 and 7 are shown in tables 1 to 4. Note that tables 3 and 4 are shown as FIGS. 3 and 4, respectively.

Based on the strategy given in the example, the following construct may also be obtained:

Triple disulfide bridges

E1 169-432 (C11-C12, C13-C14, C17-C18) as shown in SEQ ID NO: 10

EXAMPLE 2

Coupled Purification and Refolding of the SS-E1 (201-432 and 169-432) Fusion Protein All E1 chaperone fusion proteins were purified and refolded essentially according to identical protocols. *E. coli* BL21(DE3) cells harboring the expression plasmid were grown in LB medium plus kanamycin (30 μg/ml) to an $OD_{600}$ of 1, and cytosolic overexpression was induced by adding Isopropyl-β-D-Thiogalactosid (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 100 mM sodium phosphate pH 8.0, 7.0 M GuHCl, 10 mM imidazole at room temperature and the resulting suspension was stirred to complete cell lysis for two hours. After centrifugation and filtration, the lysate was applied onto a Ni-NTA (nickel-nitrilo-triacetate) column pre-equilibrated in the aforementioned lysis buffer. In order to prevent premature disulfide bridging and disulfide shuffling, 5 mM TCEP was included in the washing buffer as a reducing agent which is compatible with metal chelate columns. After an excessive washing step (>20 column volumes of lysis buffer+TCEP), the chaotropic lysis buffer was displaced by 50 mM sodium phosphate pH 7.8, 100 mM sodium chloride, 5 mM TCEP in order to induce the conformational refolding of the matrix bound protein (at least 10 column volumes of refolding buffer were applied to make sure there was no residual GuHCl in chaotropic concentrations). Subsequently, the oxidative folding (i.e. the oxidative bridging of the cysteine residues) was induced by washing with 50 mM sodium phosphate pH 7.8, 100 mM sodium chloride. Due to the high effective concentration of divalent $Ni^{2+}$ ions, the formation of disulfide bridges within the matrix-bound fusion protein is a very fast process. Prior to elution, the imidazole concentration was raised to 55 mM in order to remove a contaminant protein with an apparent molecular weight of ~50 kDa. The native fusion protein was then eluted by applying an imidazole gradient from 55 mM to 500 mM in 50 mM sodium phosphate pH 7.8, 100 mM sodium chloride. Protein containing fractions were assessed for purity (>95% as judged by SDS-PAGE) and pooled. Finally, the protein was subjected to size exclusion chromatography and the apparent dimer fraction was pooled, concentrated and assessed for its spectroscopic properties.

EXAMPLE 3

Coupling of Biotin and Ruthenium Moieties to SS-E1 (201-432)

The lysine e-amino groups of the recombinant rubella ectodomains were modified at protein concentrations of ~10 mg/ml with N-hydroxy-succinimide activated biotin and ruthenium labels, respectively. The label/protein molar ratio varied from 1:1 to 5:1, depending on the respective fusion protein. The reaction buffer was 150 mM sodium phosphate (pH 8.0), 50 mM NaCl, 1 mM EDTA. The reaction was carried out at room temperature for 15 minutes and stopped by adding buffered L-Lysine to a final concentration of 10 mM. After the coupling reaction, unreacted free label was removed by passing the crude protein conjugate over a gel filtration column (Superdex 200 HI Load).

EXAMPLE 4

Assessment of the Immunological Reactivity of the Recombinant Rubella E1 Fusion Protein SS-E1 (aa201-432) in an Immunodiagnostic Test; Detection of Anti-Rubella IgG Antibodies in Human Sera The immunological reactivity of the different fusion proteins was assessed in an automated ELECSYS 2010 analyzer (Roche Diagnostics GmbH). Measurements were carried out in the double antigen sandwich format. Thereby, the biotin-conjugate (i.e. the capture antigen) is immobilized on the surface of a streptavidin-coated magnetic bead, whereas the detection-antigen bears a complexed ruthenium cation as the signaling moiety. Signal detection in ELECSYS 2010 is based on electrochemiluminescence.

In the presence of a specific immunoglobulin analyte, the chromogenic ruthenium complex is bridged to the solid phase and emits light at 620 nm after excitation at a platinum electrode. The signal output is in arbitrary light units. Measurements were performed with anti-rubella IgG positive samples from sera panels of the Bavarian red cross.

EXAMPLE 5

FPLC Analysis (Fast Protein Liquid Chromatography Analysis)

Besides its antigenicity, the oligomeric state, the solubility and the stability of the SS-E1 fusion protein determine its suitability for diagnostic purposes. For length optimization, cysteine-free variants of E1 N-fragments (amino acids 1-314) and C-fragments (amino acids 315-432) were cloned, expressed and purified (as fusion proteins with tandem SlyD*). In order to elucidate the apparent oligomeric state of the recombinant rubella ectodomain fragments, the rubella E1 N-fragments and C-fragments were subjected to analytical gel filtration on a Superdex 200 HR 10/30 column. The running buffer was 50 mM potassium phosphate pH 7.5, 100 mM KCl. About 200 μl of the SS-E1 solution (protein concentration 1.0 mg/ml) were applied onto the SEC column, and elution was monitored via absorption at 280 nm.

The E1 N-fragments 1-55, 1-104, 1-133 and 1-142 all eluted in the separation range of the Superdex 200 column, as well as the E1 C-fragments 169-432, 201-432, 260-432 and 315-432. All the SlyD*-SlyD*-E1 variants eluted at the position of about twice the molecular size expected, suggesting apparent dimers.

EXAMPLE 6

Examination of the Immunological Reactivity of the Rubella E1 C-Fragment 201-432 with Single Disulfides in an Immunodiagnostic Test; Detection of Anti-Rubella IgG Antibodies in Human Sera The immunological reactivity of the different fusion proteins was assessed in an automated ELECSYS 2010 analyzer (Roche Diagnostics GmbH). Measurements were carried out in the double antigen sandwich format. Thereby, the biotin-conjugate (i.e. the capture antigen) is immobilized on the surface of a streptavidin-coated magnetic bead, whereas the detection-antigen bears a complexed ruthenium cation as the signaling moiety. Signal detection in ELECSYS 2010 is based on electrochemiluminescence. In the presence of a specific immunoglobulin analyte, the chromogenic ruthenium complex is bridged to the solid phase and emits light at 620 nm after excitation at a platinum electrode. The signal output is in arbitrary light units. Measuring was performed with anti-rubella IgG positive samples from sera panels of the Bavarian Red Cross. The results are shown in Table 1.

TABLE 1

Detection of anti-rubella IgG antibodies in human sera by using rubella SS-E1(aa201-432) Antigen bearing single disulfides or no disulfide

| | C13-C14 | C17-C18 | C19-C20 | no disulfide |
|---|---|---|---|---|
| rubella negative sera average counts | 2,076 | 1,453 | 2,487 | 2,076 |
| rubella positive sera | relative signal | relative signal | relative signal | relative signal |
| BRK 01/2003_115 | 23.55 | 34.88 | 17.94 | 18.17 |
| BRK 01/2003_116 | 17.09 | 7.96 | 5.83 | 4.37 |
| BRK 01/2003_119 | 13.47 | 1.89 | 5.92 | 0.94 |
| BRK 01/2003_123 | 10.30 | 5.72 | 6.66 | 4.10 |
| BRK 01/2003_127 | 11.82 | 3.37 | 2.93 | 1.82 |
| BRK 01/2003_130 | 12.81 | 2.37 | 1.58 | 1.46 |
| BRK 01/2003_157 | 3.09 | 3.33 | 2.35 | 1.73 |
| BRK 01/2003_159 | 2.31 | 1.79 | 1.14 | 0.91 |
| BRK 01/2003_162 | 15.34 | 16.58 | 11.68 | 7.70 |
| BRK 01/2003_166 | 7.12 | 2.96 | 1.64 | 1.44 |

The immunoassays were performed by using an ELECSYS 2010 analyzer as described in Example 6. The relative signals are normalized relative to the average value obtained for 7 rubella-negative samples. The rubella-positive sera were purchased from the Bavarian Red Cross, Germany, the rubella-negative controls were purchased from Trina International Bioreactives AG, Switzerland. All E1 variants were soluble SlyD*-SlyD* fusion proteins, their respective disulfide bonds are indicated in the table. All sera classified as positive were confirmed as being correct.

As obvious from Table 1 the relative signal considerably increases when the rubella E1 antigen contains a disulfide bridge whereas the signal is relatively low when the E1 antigen lacks any disulfide bridge. Introduction of a single disulfide bond within the E1 201-432 fragment significantly increases the immunological activity, probably by stabilizing conformational epitopes, which are important for immunoglobulin binding. This is true for each of the single disulfide bonds Cys 225-Cys 235, Cys 349-Cys 351 and Cys 368-Cys 401. However, the immunoreactivity, i.e., the antigenicity of rubella E1 201-432 is especially increased upon restoration of the disulfide bond Cys 225-Cys 235 (C13-C14), which probably reflects the central role of this disulfide-stabilized epitope in eliciting anti-E1 antibodies (see Table 1).

EXAMPLE 7

Examination of the Immunological Reactivity of the Rubella E1 C-fragment 201-432 with Multiple Disulfide Combinations in an Immunodiagnostic Test; Detection of Anti-Rubella IgG Antibodies in Human Sera Assessment of three different rubella-E1 variants, forming two disulfide bridges between cysteines Cys 349-Cys 352 (C17-C18) and Cys 368-Cys 401 (C19-C20) as known from EP-A-1780282 (left column), a variant according to the invention bearing two disulfide bridges between cysteines Cys 225-Cys 235 (C13-C14) and Cys 349-Cys 352 (C17-C18) (middle column) and a variant containing three disulfide bridges between cysteines Cys 225-Cys 235 (C13-C14), Cys 349-Cys 352 (C17-C18) and Cys 368-Cys 401 (C19-C20) (right column).

Measurements were performed with samples (from WHO-standard) and anti-rubella IgG positive samples from sera panels of the Bavarian Red Cross. Measurements were carried out in an automated ELECSYS 2010 analyzer (Roche Diagnostics GmbH) using the double antigen sandwich format as described in Example 6. The results are shown in Table 2.

TABLE 2

Detection of anti-rubella IgG antibodies in human sera by using rubella SS-E1(aa201-432) antigen bearing double and triple disulfide combinations.

| | C17-C18 C19-C20 | C13-C14 C17-C18 | C13-C14 C17-C18 C19-C20 |
|---|---|---|---|
| rubella-negative sera average counts | 2,830 | 2,072 | 4,610 |
| rubella positive sera | relative signal | relative signal | relative signal |
| BRK 01/2003_115 | 22.77 | 42.92 | 22.98 |
| BRK 01/2003_116 | 33.22 | 51.67 | 36.12 |
| BRK 01/2003_119 | 44.22 | 89.58 | 45.90 |
| BRK 01/2003_123 | 78.60 | 71.99 | 73.62 |
| BRK 01/2003_127 | 37.56 | 42.14 | 37.83 |
| BRK 01/2003_130 | 9.61 | 28.88 | 16.24 |
| BRK 01/2003_157 | 17.87 | 20.23 | 16.49 |
| BRK 01/2003_159 | 14.59 | 18.92 | 14.01 |
| BRK 01/2003_162 | 31.25 | 53.29 | 31.06 |
| BRK 01/2003_166 | 9.16 | 17.55 | 11.70 |

The immunoassays were performed by using an ELECSYS 2010 analyzer as described in Examples 6 and 7. The relative signals are normalized relative to the average value obtained for 7 rubella-negative samples. The rubella-positive sera were purchased from the Bavarian Red Cross, Germany, the rubella-negative controls were purchased from Trina International Bioreactives AG, Switzerland. All E1 variants were soluble SlyD*-SlyD* fusion proteins, their respective disulfide bond combinations are indicated in the table. All sera classified as positive were confirmed as being correct.

As can be seen from table 2, all E1 variants are reactive in the immunoassay, i.e., the antigens specifically bind to anti-rubella antibodies in the samples. Surprisingly, the immunological activity (i.e. the antigenicity) is strongly increased when a second disulfide bond is added. This increase is cooperative rather than additive, i.e., the signal contributions of the single disulfide bond variants do not simply add up to yield the overall signal. Instead, the overall signal is significantly higher than the sum of the individual signals generated by the single disulfide bond constructs (see Table 2).

This marked signal increase upon restoration of two disulfide bridges holds true for all variants tested. However, the signal height turns out to be different for the distinct two-disulfide constructs. For instance, E1 201-432 with the disulfide bond combination Cys 225-Cys 235 and Cys 349-Cys 351 (C13-C14 and C17-C18) turns out to be an excellent antigen, which is well suited for the detection of anti-E1 immunoglobulins in human sera (see Table 2). In 9 out of 10 samples this variant with two disulfide bridges according to the invention (C13-C14 and C17-C18, middle column) shows a considerably higher signal than the double disulfide variant known in the prior art (C 17-C18 and C19-C20) and the triple bridge variant in the right column. It can be shown that the rubella E1 antigens according to the invention are well suited for being used as antigens in an immunoassay for the detection of anti-rubella antibodies in a human sample.

Further Description to Tables 1 and 2 and Tables 3 (FIG. 3) and 4 (FIG. 4)

The results shown in Tables 3 and 4 confirm the results of tables 1 and 2, respectively, i.e., the relative signal substantially increases as soon as the rubella E1 antigen contains a combination of two disulfide bridges whereas the signal is rather poor when the E1 antigen bears only one disulfide bridge or is completely devoid of cysteine residues.

Restoration of a single disulfide bond within the E1 201-432 fragment (Table 3) slightly increases the immunological activity. Best results are obtained with the single disulfide bond Cys 225-Cys 235 (C13-C14). Introduction of an additional disulfide bond, in particular the combination of the disulfide bridges C17-C18 and C19-C20 as well as the combination of the disulfide bridges C13-C14 and C17-C18 results in a significant increase of the signal. The addition of a third disulfide bridge does, however, not further contribute significantly to the signal.

Table 4 shows that the restoration of the single disulfide bond Cys 176-Cys 185 (C11-C12) within the E1 169-432 fragment does barely alter the immunological activity. However, in combination with one of the other disulfide bridges, the C11-C12 disulfide bridge significantly increases the signal. The respective double disulfide construct exhibits an immunoreactivity that clearly exceeds the sum of the reactivities of the single disulfide constructs, which is indicative of a cooperative mode of action. Best results are obtained by combining the disulfide bridges C11-C12 and C13-C14, followed by the combination of the disulfide bridge C11-C12 with C19-C20 and C11-C12 with C17-C18. Also the combination of disulfide bridges C13-C14 with C19-C20 within the rubella E1 antigen leads to an excellent immunological reactivity as reflected in high relative signals. A significant increase in the signal is also observed when the apparently inert single disulfide bridge C11-C12 is added to the double disulfide combination C17-C18/C19-C20 to yield the triple disulfide construct C11-C12/C17-C18/C19-C20. Remarkably, the immunoreactivity of this triple disulfide E1 construct exceeds the added up immunoreactivities of the single (C11-C12) and the double disulfide construct (C17-C18/C19-C20), again indicative of a cooperative mode of action.

To sum up, the disulfide bridge Cys 176-Cys 185 (C11-C12), when taken alone, does not conspicuously contribute to the immunological reactivity (i.e. antigenicity) of the rubella E1 antigen. However, as soon as the seemingly inert single disulfide bridge Cys 176-Cys 185 (C11-C12) is combined with at least one of the other disulfide bridges, this combination surprisingly leads to a cooperatively improved antigen with excellent immunological reactivity. E1 variants bearing the C11-C12 disulfide bridge in combination with either the disulfide bridge C13-C14 or C17-C18 or C19-C20 or bearing the C11-C12 disulfide bridge in combination with both the disulfide bridge C17-C18 and C19-C20 are excellent tools for the detection of anti-rubella E1 antibodies in human sera.

What is claimed is:

1. A rubella E1 antigen comprising amino acids 201 to 432 with the proviso that said antigen lacks sequences corresponding to amino acids 143 to 164 and 454 to 481 of the native rubella E1 antigen and containing a first disulfide bridge formed between Cys 225 and Cys 235 (C13-C14) and a second disulfide bridge formed between only one of Cys 349 and Cys 352 (C17-C18) or Cys 368 and Cys 401 (C19-C20).

2. A rubella E1 antigen comprising amino acids 169 to 432 with the proviso that said antigen lacks sequences corresponding to amino acids 143 to 164 and 454 to 481 of the native rubella E1 antigen and containing a first disulfide bridge formed between Cys 176 and Cys 185 (C11-C-12) and a second disulfide bridge formed between only one of Cys 349 and Cys 352 (C17-C18) or Cys 368 and Cys 401 (C19-C20).

3. The rubella E1 antigen according to claim 1 wherein said antigen is fused with a peptidyl-prolyl-isomerase class chaperone.

4. The rubella E1 antigen according to claim 2 wherein said antigen is fused with a peptidyl-prolyl-isomerase class chaperone.

5. A reagent kit for the detection of antibodies against rubella containing a rubella E1 antigen according to claim 1.

6. A reagent kit for the detection of antibodies against rubella containing a rubella E1 antigen according to claim 2.

7. A composition comprising two different rubella E1 antigens, said composition comprising:

a first rubella E1 antigen comprising amino acids 201 to 432 with the proviso that said antigen lacks sequences corresponding to amino acids 143 to 164 and 454 to 481 of the native rubella E1 antigen and containing a first disulfide bridge formed between Cys 225 and Cys 235 (C13-C14) and a second disulfide bridge formed between only one of Cys 349 and Cys 352 (C17-C18) or Cys 368 and Cys 401 (C19-C20); and a second rubella E1 antigen comprising amino acids 169 to 432 with the proviso that said antigen lacks sequences corresponding to amino acids 143 to 164 and 454 to 481 of the native rubella E1 antigen and containing a first disulfide bridge formed between Cys 176 and Cys 185 (C11-C12) and a second disulfide bridge formed between only one of Cys 349 and Cys 352 (C17-C18) or Cys 368 and Cys 401 (C19-C20).

* * * * *